United States Patent
Nuber

(10) Patent No.: US 7,695,706 B2
(45) Date of Patent: Apr. 13, 2010

(54) PRODUCING METHOD OF FULLERENE DERIVATIVE, FULLERENE DERIVATIVE, PROTON CONDUCTOR AND ELECTROCHEMICAL DEVICE

(75) Inventor: Berthold Nuber, Kanagawa (JP)

(73) Assignee: Sony Corporation, Tokyo (JP)

( * ) Notice: Subject to any disclaimer, the term of this patent is extended or adjusted under 35 U.S.C. 154(b) by 767 days.

(21) Appl. No.: 11/427,909

(22) Filed: Jun. 30, 2006

(65) Prior Publication Data
US 2006/0239888 A1 Oct. 26, 2006

Related U.S. Application Data

(62) Division of application No. 10/451,320, filed as application No. PCT/JP01/11352 on Dec. 25, 2001, now Pat. No. 7,371,479.

(30) Foreign Application Priority Data
Dec. 25, 2000 (JP) .......................... P2000-391777

(51) Int. Cl.
*B01J 19/08* (2006.01)
(52) U.S. Cl. .................. 423/445 B; 977/734; 977/735; 977/740; 429/33
(58) Field of Classification Search ............. 423/445 B; 977/734, 735, 736, 737, 738, 739, 740, 741; 429/33
See application file for complete search history.

(56) References Cited

U.S. PATENT DOCUMENTS 6,113,673 A 9/2000 Loutfy et al.

(Continued)

FOREIGN PATENT DOCUMENTS

EP 0770577 5/1997

(Continued)

OTHER PUBLICATIONS

B.L. Tumanskii, et al., "ESR study of spin-adducts of phosphoryl radicals with methano[60]fullerenes", Russian Chemical Bulletin, 2000, vol. 49, No. 5, pp. 843-846.

(Continued)

*Primary Examiner*—Stanley S. Silverman
*Assistant Examiner*—Daniel C. McCracken
(74) *Attorney, Agent, or Firm*—Sonnenschein Nath & Rosenthal LLP

(57) ABSTRACT

Provided are a method of efficiently procuding fullerene into which a OH group or a $SO_3H$ group is introduced, such as fullerenol, or a derivative thereof, the fullerene and its derivative being preferable as a proton conductor, and a novel and usable proton conductor obtained by the method. Further, provided is an electrochemical device using the proton conductor such as a fuel cell or the like. In the producing method of the fullerene derivative, halogated fullerene, which is obtained through halogating a fullerene molecule is used as a precursor, the fullerene derivative is produced through introducing one or more proton dissociative group into at least one carbon atom of a fullerene molecule. Moreover, in a producing method of a polymerized fullerene derivative, a plurality of fullerene derivatives are bonded to one another by an aromatic group of an aromatic compound through reacting the plurality of fullerene derivatives with the aromatic compound. The fullerene derivative obtained by any of these method functions as a proton conductor, and an electrochemical device using the proton conductor such as a fuel cell can be downsized and simplified without atmosphere constraints.

8 Claims, 14 Drawing Sheets

U.S. PATENT DOCUMENTS

| | | | |
|---|---|---|---|
| 6,323,297 | B1 | 11/2001 | Lee et al. |
| 6,495,290 | B1 * | 12/2002 | Hinokuma et al. ........ 429/231.8 |
| 6,805,985 | B2 * | 10/2004 | Yamada et al. ................. 429/21 |
| 6,821,665 | B2 * | 11/2004 | Hinokuma et al. ............. 429/33 |

FOREIGN PATENT DOCUMENTS

| | | |
|---|---|---|
| EP | 1071149 | 1/2001 |
| JP | 11-258796 | 9/1999 |

OTHER PUBLICATIONS

Liming Dai, et al., "Doping of Conducting Polymers by Sulfonated Fullerene Derivatives and Dendrimers", J. Phys. Chem. B, 1998, vol. 102, No. 21, pp. 4049-4053.

Long Y. Chiang, et al., "Efficient Synthesis of Polyhydroxylated Fullerene Derivatives via Hydrolysis of Polycycloulfated Precursors", J. Org. Chem., 1994, vol. 59, No. 14, pp. 3960-3968.

Chen, et al., "Process for preparing Cy(OH)n", Database CA 'Online! Chemical Abstracts Service, Columbus, Ohio, XP002348703, Database accession No. 2002:940198 (abstract).

Boltalina, Olga, et al., "Preparation of C60F36 and C70F36/38/40", Chemical Communications (Cambridge), 529-30 Coden: CHCOFS; ISSN: 1359-7345, 1996, XP008053778 (abstract).

Birkett, Paul R.., et al., "The structural characterizatino of buckminsterfullerene compounds", Journal of Molecular Structure, 292,1-8 Coden: JM0SB4; ISSN: 0022-2860, 1993, XP002348699 (abstract).

Birkett, Paul R., et al., "Preparation and characterization of hexabromofullerene and octabromofullerene", Nature (London, UK), 357, 479-81 Coden: Natuas; ISSN: 0028-0836, 6378, XP002348700 (abstract.

Birkett, Paul R., et al., "Preparation and carbon 13 NMR spectroscopic characterization of hexachlorofullerene (C60C16)", Journal of the Chemical Society, Chemical Communications, (15), 1230-2 Coden: JCCCAT; ISSN: 0022-4936, 1993, XP008053850 (abstract).

Wang, et al., "Structures and stabilities of C60(OH)6 and C60(OH)12 fullerenols", Theochem, 391(1-2), 179-187 Coden: THEODJ; ISSN: 0166-1280, 1997, XP002348701 (p. 182.

* cited by examiner

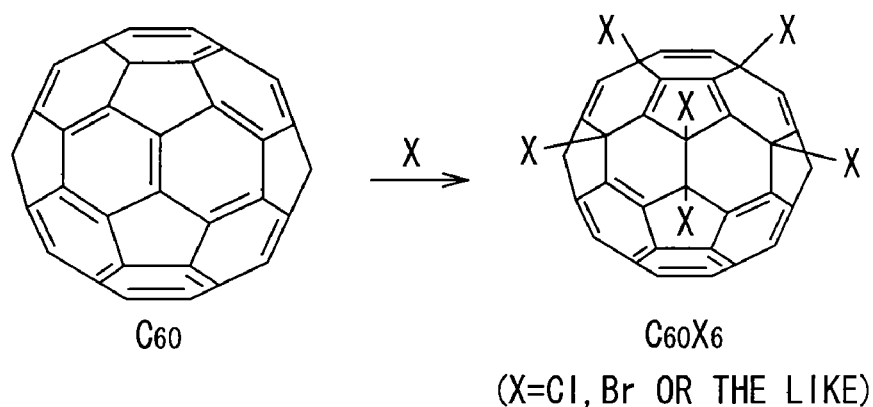
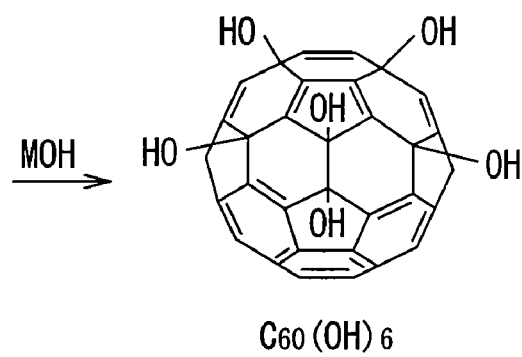
FIG. 2A
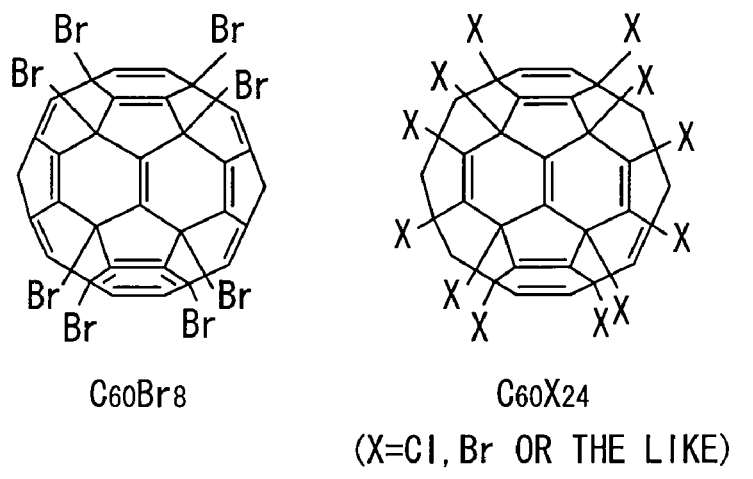
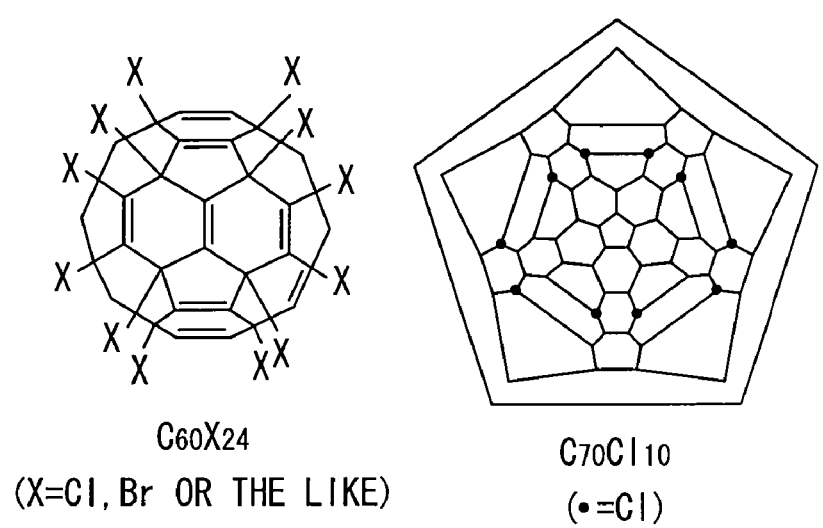
FIG. 2B     FIG. 2C     FIG. 2D $C_{60}F_{18}$ $C_{60}F_{36}$ $C_{60}F_{48}$ (•=F)

C60

C70

PRODUCING METHOD OF FULLERENE DERIVATIVE, FULLERENE DERIVATIVE, PROTON CONDUCTOR AND ELECTROCHEMICAL DEVICE

RELATED APPLICATION DATA

This application is divisional of U.S. patent application Ser. No. 10/451,320, filed Nov. 7, 2003, now U.S. Pat. No. 7,371,479, which is incorporated herein by reference to the extent permitted by law. This application claims the benefit of priority to PCT/JP01/11352 filed Dec. 25, 2001 and Japanese Patent Application No. JP 2000-391777 filed in the Japanese Patent Office on Dec. 25, 2000.

TECHNICAL FIELD

The present invention relates to a producing method of a fullerene derivative suitable for a proton (hydrogen ion; $H^+$) conducting material, the fullerene derivative, a proton conductor, and an electrochemical device.

BACKGROUND ART

Fullerene molecules $C_{60}$, and $C_{70}$ shown in FIGS. 15A and 15B were found in a mass spectrometry spectrum of a cluster beam by laser ablation of carbon in 1985 (Kroto, H. W.; Heath, J. R.; O'Brien, S. C.; Curl, R. F.; Smalley, R. E. Nature 1985.318,162.), and 5 years later in 1990, a producing method of the fullerene molecules by arc discharge method using a carbon electrode was established. Since then, attention has been focused on the fullerene molecules as a carbon-based semiconductor material or the like.

Moreover, the first example of synthesis of an compound with a structure in which a plurality of hydroxyl groups are added to at least one carbon atom of a fullerene molecule, that is, polyhydroxylated fullerene (which is commonly called "fullerenol", hereinafter referred to as fullerenol) was reported in 1992 by Chiang et al. (Chiang, L. Y.; Swirczewski, J. W.; Hsu, C. S.; Chowdhury, S. K.; Cameron, S.; Creegan, K. J. Chem. Soc, Commun. 1992, 1791 and Chiang, L. Y.; Wang, L. Y.; Swirczewski, J. W.; Soled, S.; Cameron, S. J. Org. Chem. 1994, 59, 3960). Since then, attention has been focused on fullerenol into which a certain amount or over of the hydroxyl groups is introduced, specifically its water-soluble property, and the fullerenol has been studied mainly in technical fields related to biotechnology.

Further, a compound in which the hydroxyl groups of the above-described fullerenol was replaced with sulfone groups, that is, hydrogensulfate-esterified fullerenol was reported in 1994 by Chiang et al. (Chiang, L. Y.; Wang, L. Y.; Swirczewski, J. W.; Soled, S.; Cameron, S. J. Org. Chem. 1994, 59, 3960).

FIG. 16 shows an example of a conventionally known method of synthesizing the fullerenol and the hydrogensulfate-esterified fullerenol.

In the conventionally known synthesizing method (Long Y. Chiang et al. J. Org. Chem. 1994, 59, 3960), fuming sulfuric acid is added to the fullerene molecule, then the fullerene molecule is hydrolyzed so as to obtain fullerenol $C_{60}(OH)_n$. When the fullerenol reacts with sulfuric acid, hydrogensulfate-esterified fullerenol $C_{60}(OSO_3H)_n$ is produced.

In recent years, for example, as a solid high molecular weight electrolyte type fuel cell for a vehicle's power source, a fuel cell using a proton (hydrogen ion; hereinafter referred to as the same) conducting high molecular weight material such as perfluorosulfonic acid resin (Nafion(R) of Du Pont or the like) is well known.

Moreover, as a relatively novel proton conductor, a polymolybdic acid containing a large amount of hydrated water such as $H_3Mo_{12}PO_{40}.29H_2O$, or an oxide containing a large amount of hydrated water such as $Sb_2O_5.5.4H_2O$ or the like is well known.

When the high molecular weight material and the hydrated compounds are placed in a wet state, they exhibit high proton conductivity at about room temperature. In other words, when the perfluorosulfonic acid resin is taken as an example, protons ionized from a sulfonic acid group of the perfluorosulfonic acid resin are bonded (hydrogen-bonded) to water contained in, for example, a high molecular weight matrix of the solid high molecular weight electrolyte in a large amount, to produce protonated water, that is, oxonium ions ($H_3O^+$), and protons in the form of oxonium ions can smoothly move in the high molecular weight matrix, so a matrix material of this kind can exert a very high proton conduction effect even at room temperature.

On the other hand, recently, a proton conductor with a conduction mechanism completely different from those of the above proton conductors has been also developed. More specifically, it has been found that a composite metal oxide with a perovskite structure such as $SrCeO_3$ doped with Yb or the like can conduct protons without using water as a transfer medium. It has been considered that in the composite metal oxide, protons are singly channeled between oxygen ions forming a framework of the perovskite structure so as to be conducted.

In this case, conductive protons are not originally present in the composite metal oxide. When the perovskite structure is in contact with water vapor contained in an ambient atmospheric gas, water molecules at high temperature react with an oxygen deficient portion formed in the perovskite structure by doping, and the protons are generated only by the reaction.

However, the above described various proton conductors have the following problems.

Firstly, in order to maintain high proton conductivity, the matrix material such as the perfluorosulfonic acid resin is required to be continuously placed in a wet state during use. Therefore, a humidifier or various accompanying apparatuses are required to be mounted in the entire structure of a system such as fuel cell or the like, so an increase in the size of the system and cost for system configuration is inevitable.

Moreover, the operating temperature of the system is limited to a range in which freezing and boiling of water contained in the matrix do not occur, so there is a problem that it is difficult to have a wider temperature range.

Further, in the case of the composite metal oxide with the perovskite structure, in order that meaningful proton conduction is carried out, the operating temperature is required to be maintained at 500° C. or over.

As described above, the conventional proton conductors have the following problems. The conventional proton conductor has high dependence on atmosphere, and more specifically, moisture must be supplied to the proton conductor, or the proton conductor requires water vapor. Further, the range of the operating temperature is narrow, or the operating temperature is too high.

Therefore, the applicant of the present invention has found that, as described above, fullerenol and hydrogensulfate-esterified fullerenol exhibit proton conductivity, and has proposed novel proton conductors (hereinafter referred to as inventions disclosed in the prior applications) in Japanese Patent Application No. Hei 11-204038 and 2000-058116.

The proton conductors according to the inventions disclosed in the prior applications can be used in a wide temperature range including room temperature, and a lower limit of the temperature range is not specifically high. Further, the proton conductors do not require water as a transfer medium. Therefore, the proton conductors have achieved a reduction in dependence on atmosphere, and an increase in an applicable range.

There are two following factors which control proton conductivity of fullerenol and hydrogensulfate-esterified fullerenol.

One of the factors is a structural aspect. It is considered that a proton transfer phenomenon occurs by quantum channeling effects, so fullerenol and hydrogensulfate-esterified fullerenol preferably have a tightly packed solid structure, because (1) the quantum channeling effects are highly dependent on a distance between each site which transfers protons, (2) when fullerenol and hydrogensulfate-esterified fullerenol have a tightly packed solid structure, a more stable thin film can be formed, thereby a thinner layer with high conductance can be supplied, and (3) a loss of $H_2$ in a proton conducting layer is reduced by diffusion of $H_2$.

The other factor is the number of sites which transfer protons. An important factor which controls conductance is the number of charged carriers which can be used for proton transfer. Therefore, an improvement in proton conductance can be expected by increasing the number of proton transfer sites in the proton conducting layer.

However, in the above-described conventional method of synthesizing fullerenol and hydrogensulfate-esterified fullerenol, the following problems arise. Namely, when the hydroxyl groups are added to a fullerene molecule, the position of the hydroxyl groups introduced into at least one carbon atom of the fullerene molecule cannot be controlled, and the number of the hydroxyl groups introduced into the fullerene molecule cannot be controlled (12 hydroxyl groups per fullerene molecule is a limit).

In view of the foregoing, it is a first object of the invention to provide a method of efficiently producing fullerene into which a hydroxyl group is introduced and which is suitable as a proton conductor, such as fullerenol, or a derivative thereof.

It is a second object of the invention to provide a novel and useful fullerene derivative obtained by the method, a proton conductor, and an electrochemical device using the proton conductor.

DISCLOSURE OF THE INVENTION

The present invention provides a producing method of a fullerene derivative (hereinafter referred to as a first producing method of the invention), which comprises the steps of: reacting a fullerene molecule with at least one halogen atom so as to produce a halogenated fullerene; and reacting the halogenated fullerene with a hydroxide or sulfite so as to produce a fullerene derivative, wherein one or more proton ($H^+$) dissociative group is introduced into at least one carbon atom of the fullerene molecule.

The invention also provides a producing method of a fullerene derivative (hereinafter referred to as a second producing method of the invention), which comprises the steps of: reacting a fullerene molecule with at least one halogen atom so as to produce halogenated fullerene; and reacting the halogenated fullerene with an aromatic compound having one or more proton ($H^+$) dissociative group by exchange reaction specifically in the presence of a Lewis acid catalyst so as to produce a fullerene derivative, wherein one or more aromatic group having one or more proton ($H^+$) dissociative group is introduced into at least one carbon atom of the fullerene molecule.

Herein, "a proton dissociative group" in the invention means a functional group in which a proton can be dissociated by ionization, and "proton ($H^+$) dissociation" means that a proton is dissociated from the functional group by ionization.

According to the first and the second producing methods of the invention, halogenated fullerene as a precursor is produced by a reaction between a fullerene molecule and halogen, and by use of the precursor, a fullerene derivative such as fullerenol is produced. Therefore, compared to a method of directly synthesizing fullerenol from a fullerene molecule, such as the above described conventionally known method, while dependence on properties of halogen and its position are exhibited, the number of hydroxyl groups added to the fullerene molecule or the positions of the hydroxyl groups can be controlled, thereby, a derivative suitable for proton conducting material can be obtained.

In addition, by using the above halogenated fullerene, the number of the above introduced group in an aromatic compound which will be reacted with the halogenated fullerene can be increased, so hydroxylation of fullerene or the like can be carried out to a high degree. Thereby, the number of charged carriers which can be used for proton transfer can be increased, and the number of proton transfer (or migration) site can be increased, and accordingly, proton conductance can be improved.

The invention provide a producing method of a polymerized fullerene derivative (hereinafter referred to as a third producing method of the invention), which comprises the steps of: reacting a fullerene molecule with at least one halogen atom so as to produce halogenated fullerene; reacting the halogenated fullerene or a derivative thereof with a first aromatic compound having one or more proton ($H^+$) dissociative group and a second compound by exchange reaction especially in the presence of a Lewis acid catalyst so as to produce a fullerene derivative, wherein one or more aromatic group of the first aromatic compound having one or more proton ($H^+$) dissociative group is introduced into at least one carbon atom of the fullerene molecule; and bonding a plurality of the fullerene derivatives obtained thereby to one another by one or more aromatic group of the second aromatic compound so as to produce a polymerized fullerene.

According to the third producing method of the invention, as in the case of the first and the second producing methods of the invention, by using the halogenated fullerene, the aromatic compound having the proton ($H^+$) dissociative group is introduced into the fullerene molecule, and the fullerene is polymerized through bonding fullerene molecules to one another by the aromatic group, so while the positions and the number of transfer sites for proton conduction are preferably controlled, a decline in the strength of the fullerene derivative due to addition of a group such as a hydroxyl group can be fully compensated by polymerization, therefore, a thin film with larger strength can be formed.

The invention related to a fullerene derivative (hereinafter referred to as a first fullerene derivative of the invention), wherein one or more aromatic group having a proton ($H^+$) dissociative group introduced into at least one carbon atom of a fullerene molecule.

As described above, in the first fullerene derivative of the invention, the proton dissociative group is introduced by the aromatic group, so the number of proton transfer sites can be increased, and the positions of proton transfer sites can be controlled.

The invention provides a polymerized fullerene derivative (hereinafter referred to as a second fullerene derivative of the invention), wherein in a fullerene derivative, one or more first aromatic group having one or more proton ($H^+$) dissociative group is introduced in at least one carbon atom of a fullerene molecule, and a plurality of the fullerene derivatives are bonded to one another by a second aromatic group so as to produce a polymerized fullerene derivative.

In other words, in the second fullerene derivative of the invention, in addition to having advantages of the first fullerene derivative of the invention, the fullerene molecule is polymerized, so a thin film with larger strength as described above can be formed.

The first and the second fullerene derivatives can form a first proton conductor and a second proton conductor of the invention, respectively. The first proton conductor of the invention can be substantially formed of the fullerene derivative only in a thin film through, for example, compression molding, or can be formed of fullerene derivatives bonded by a binder in a thin film. Moreover, the second proton conductor of the invention uses the polymerized fullerene derivative, so the proton conductor has been already polymerized. Therefore, the proton conductor can be formed in a thin film with larger strength without using a binder.

In the first and the second fullerene derivatives of the invention and the first and the second proton conductors of the invention, as in the case of the above-described inventions disclosed in the prior applications, the proton dissociative group is introduced into the fullerene molecule, so they become proton conductors with smaller atmosphere dependence, which can be used within a wider temperature range including room temperature and have the lower limit being not specifically high, and which do not require water as a transfer medium (however, water may be present therein).

The invention further provides an electrochemical device (hereinafter referred to as an electrochemical device of the invention), which comprises a first electrode, a second electrode and a proton conductor sandwiched between the first electrode and the second electrode, wherein the proton conductor comprises either the following (1) or (2).

The proton conductor comprises (1) a fullerene derivative as a main component, wherein one or more aromatic group having one or more proton ($H^+$) dissociative group is introduced into at least one carbon atom of a fullerene molecule (that is, the first proton conductor of the invention).

Alternatively, the proton conductor comprises (2) a polymerized fullerene derivative, wherein in a fullerene derivative, one or more first aromatic group having one or more proton ($H^+$) dissociative group is introduced in at least one carbon atom of a fullerene molecule, and a plurality of the fullerene derivatives are bonded to one another by a second aromatic group so as to produce the polymerized fullerene derivative (that is, the second proton conductor of the invention).

Thus, the electrochemical device of the invention comprising the first or the second proton conductor of the invention is not subject to atmosphere constraints, so downsizing and simplification of the system thereof can be achieved.

Other and further objects, features and advantages of the invention will appear more fully from the following description.

BRIEF DESCRIPTION OF THE DRAWINGS

FIGS. 2A through 2D are illustrations showing the first producing method of the invention and examples of a fullerene derivative obtained by the first producing method;

BEST MODE FOR CARRYING OUT THE INVENTION

Figure 15A:
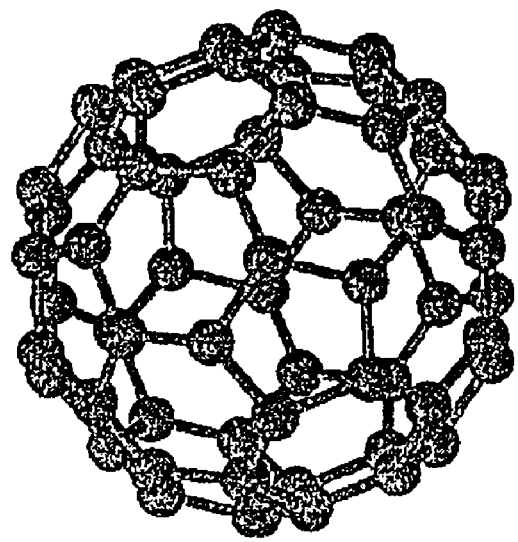
FIGS. 15A and 15B are structure diagrams of a fullerene molecule.
Figure 15B:
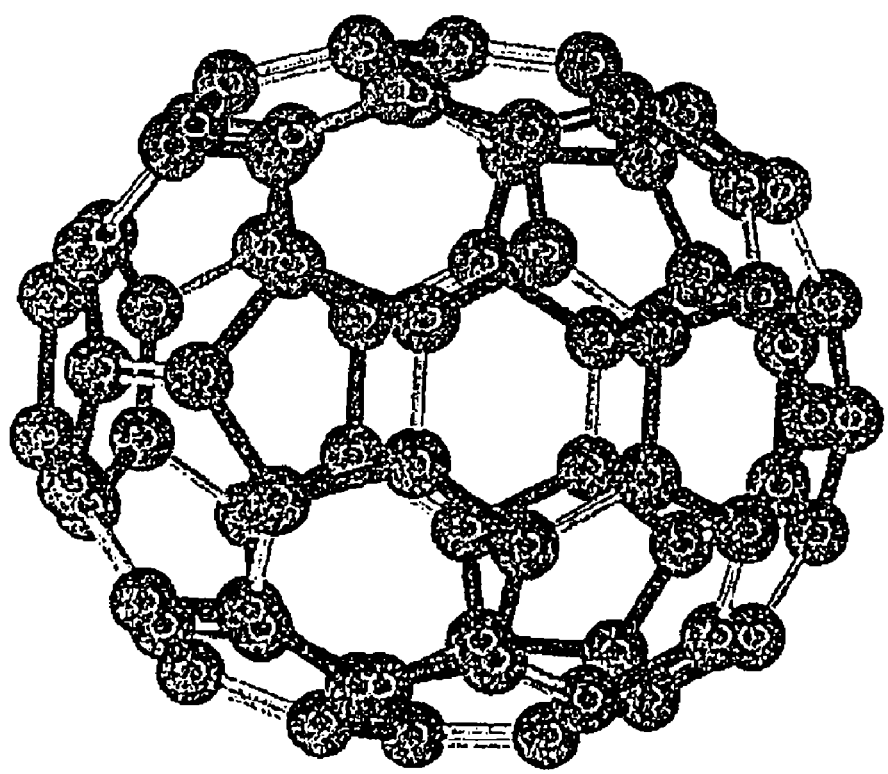
Figure 16:
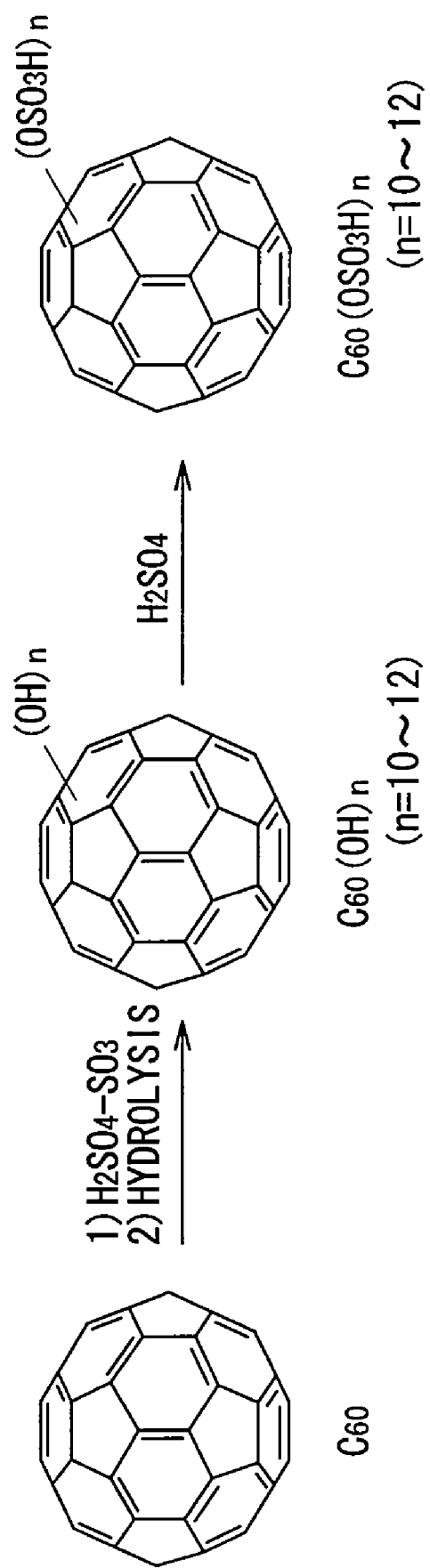
FIG. 16 is an illustration showing a conventionally known producing method of a fullerene derivative.

In the present invention, a fullerene molecule as a base into which one or more proton dissociative groups are introduced is not specifically limited, as long as the fullerene molecule is a spherical carbon cluster molecule Cm. However, in general, a fullerene molecule selected from the group of fullerene molecules $C_{36}$, $C_{60}$ (refer to FIG. 15A), $C_{70}$ (refer to FIG. 15B), $C_{76}$, $C_{78}$, $C_{80}$, $C_{82}$, $C_{84}$ and so on or a mixture of two or more kinds selected from the fullerene molecules is preferably used.

Next, examples of a fullerene derivative of the invention and a producing method thereof will be described below.

Figure 1:
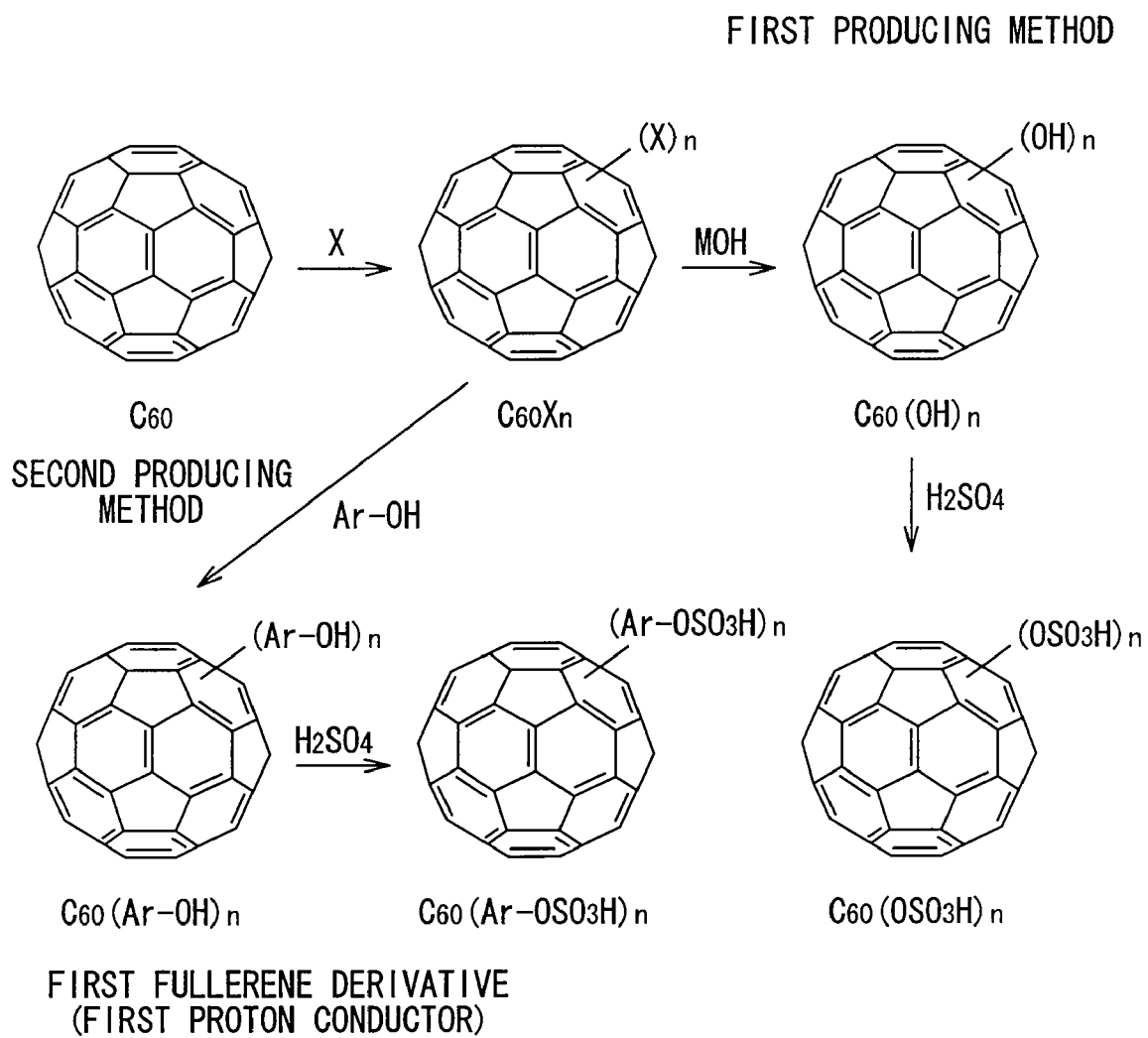
FIG. 1 shows a first producing method and a second producing method of the invention and examples of a fullerene derivative obtained by the methods.

FIG. 1 shows an example of a first producing method of the invention. In the method, for example, a fullerene molecule (for example, $C_{60}$) is reacted with at least one halogen atom X to produce halogenated fullerene $C_{60}X_n$, and the halogenated fullerene is reacted with hydroxide MOH (that is, nucleophilic substitution reaction) so as to produce a fullerene derivative ($C_{60}(OH)_n$, $C_{60}(OSO_3H)_n$ which is $C_{60}(OH)_n$ sulfonated by sulfuric acid, or the like) having one or more proton dissociative group (for example, —OH, —OSO$_3$H, —SO$_3$H or the like) in at least one carbon atom of the fullerene molecule, as a proton conductor.

Moreover, in the first producing method (not shown) according to the invention, for example, $C_{60}X_n$ as the above-described halogenated fullerene and sulfite $M_2SO_3$ are reacted with each other so as to produce a fullerene derivative (for example, $C_{60}(SO_3H)$, or the like) having one or more SO$_3$H group as the proton dissociative group in at least one carbon atom of the fullerene molecule, as a proton conductor.

As the halogen atom X used herein, a halogen atom selected from the group consisting of a fluorine atom (F), a chlorine atom (Cl) and a bromine atom (Br) are preferable (hereinafter the same). These halogen atoms can be supplied by a fluorine compound, bromine or the like, as described later.

As the above-described halogenated fullerene, brominated fullerene, chlorinated fullerene and fluorinated fullerene are listed in order of increasing stability and increasing solubility.

As the halogenated fullerene, fluorinated fullerene and chlorinated fullerene are more preferably used as a precursor. Fluorinate fullerene or chlorinated fullerene easily induces a nucleophilic substitution reaction, and the order of decreasing nucleophilic substitution reactivity is C—F>C—Cl>C—Br. It is effective to determine reaction conditions based upon such reactivity, because the structure of fullerenol or a derivative thereof can be determined depending upon the kind of a precursor of each halogenated fullerene.

Figure 3A:
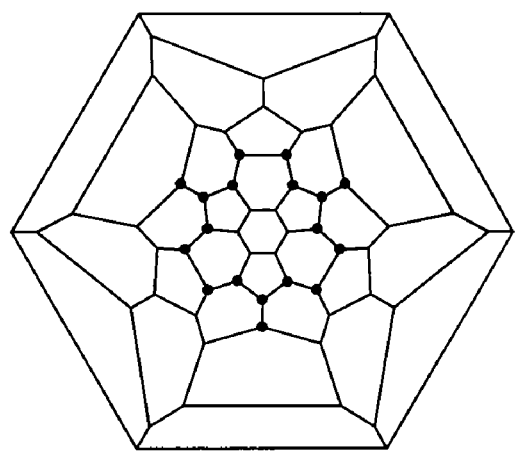
FIGS. 3A through 3C are illustrations showing examples of fluorinated fullerene as halogenated fullerene (precursor) in the first producing method of the invention.
Figure 3B:
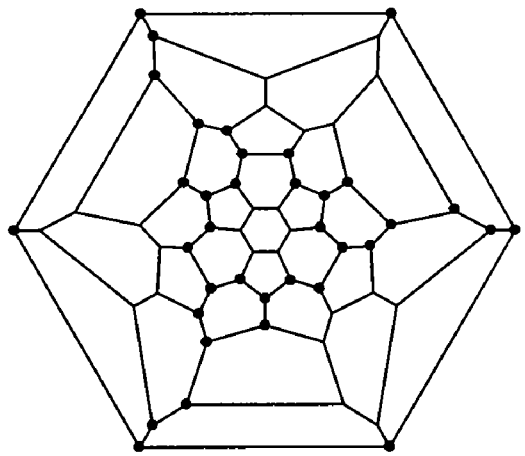
Figure 3C:
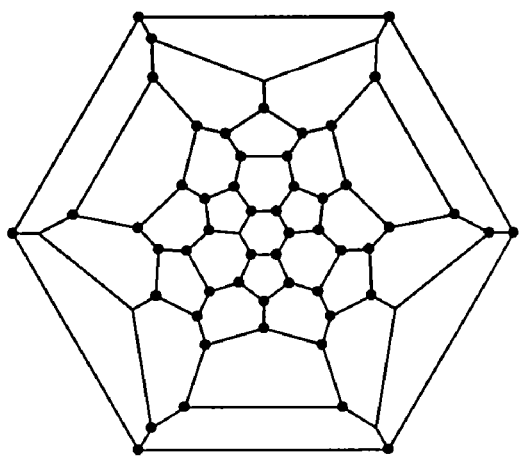

FIGS. 2A through 2D show examples of halogenation of a fullerene molecule, and show examples of chlorinated fullerene and brominated fullerene, that is, $C_{60}Cl_6$, $C_{60}Br_6$, $C_{60}Br_8$, $C_{60}Cl_{24}$ and $C_{60}Br_{24}$. FIGS. 3A through 3C show examples of fluorinated fullerene, that is, $C_{60}F_{18}$, $C_{60}F_{36}$ and $C_{60}F_{48}$ (in the case of $C_{70}$, $C_{70}F_{36-40}$ in general). Some of these halogenated fullerenes are produced as a main component, but in general, the halogenated fullerenes are produced as a mixture.

M in the above hydroxide MOH or the above sulfite $M_2SO_3$ is preferably an alkali metal atom selected from the group consisting of Li, Na and K.

A reaction between the above halogenated fullerene and the above hydroxide is preferably carried out in an inert organic solvent such as o-dichlorobenzene or the like, and the above organic solvent to which at least one of crown ether and a Lewis acid catalyst ($AlCl_3$, $FeCl_3$, $TiCl_4$ or the like) is added is more preferable. As the above Lewis acid catalyst, a catalyst selected from the group consisting of $AlCl_3$, $FeCl_3$ and $TiCl_4$ can be used.

Moreover, the reaction between the above halogenated fullerene and the above hydroxide can be carried out in a two-phase system of the above hydroxide solution and the above organic solvent by using at least one of a phase-transfer catalyst such as $NBu_4OH$ or the like and the Lewis acid catalyst (the same as above) at room temperature or a raised temperature. In some cases (for example, in the case where fluorinated fullerene is used), hydroxylation can be carried out through reacting with water.

Further, hydroxylated fullerene (fullerenol) can be obtained by a reaction between the above halogenated fullerene and the above hydroxide, and the hydroxylated fullerene can be further sulfonated (—$OSO_3H$ can be introduced into the hydroxylated fullerene) by sulfuric acid, or phosphatized (—$OPO(OH)_2$ can be introduced into the hydroxylated fullerene) by phosphoric acid. The sulfonated fullerene has an advantage that the sulfonated fullerene has higher proton conductivity than fullerenol.

Further, an example of a first fullerene derivative (or a first proton conductor) obtained by a second producing method of the invention as described above is also shown in FIG. 1.

The second producing method of the invention is a producing method of a fullerene derivative as a proton conductor, in which by a nucleophilic substitution reaction between the halogenated fullerene produced based upon the above-described first producing method of the invention and an aromatic compound having one or more proton dissociative group, one or more aromatic group having the above proton dissociative group is introduced into at least one carbon atom of the above fullerene molecule.

A Lewis acid catalyst which can be used in the second producing method of the invention is not specifically limited, and, for example, a catalyst selected from the group consisting of $AlCl_3$, $FeCl_3$ and $TiCl_4$ is cited. In the presence of the Lewis acid catalyst, the halogenated fullerene forms a carbocation, and an electrophilic substitution reaction between the carbocation and an aromatic compound such as phenol or the like can occur. The substitution reaction selectively occurs in a position where the halogen atom of the fullerene molecule is introduced, and aromatic group substituted fullerene corresponding to halogenated fullerene can be reliably obtained.

The above group which can dissociate the above proton may be selected from the group consisting of —OH, —$OSO_3H$, —COOH, —$SO_3H$ and —$OPO(OH)_2$ (hereinafter the same).

The above aromatic compound or a mixture of the aromatic compound and other solvent (for example, o-dichlorobenzene) can be used as a solvent.

Moreover, the above aromatic group added to the fullerene molecule may be, for example, an aryl group such as a phenol group, and an aromatic compound having one, or two or more hydroxyl groups in one aromatic ring (for example, resorcinol) may be used. When an aromatic compound having two or more hydroxyl groups or the like is used, proton transfer sites can be easily increased.

Figure 4A:
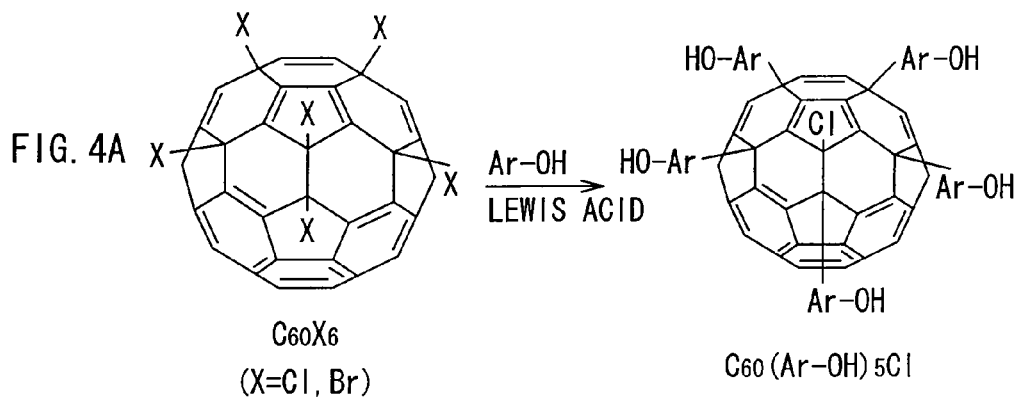
FIGS. 4A through 4C are illustrations showing the first producing method of the invention and examples of the fullerene derivative obtained by the first producing method.
Figure 4B:
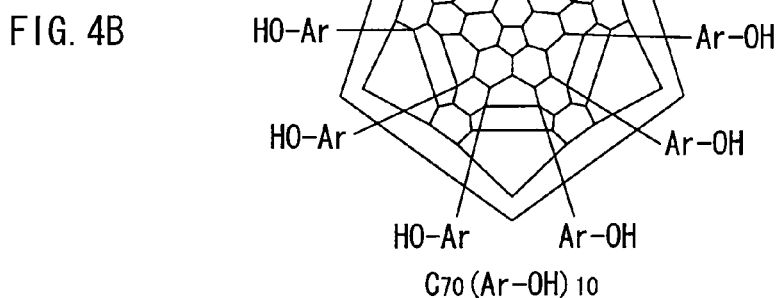
Figure 4C:
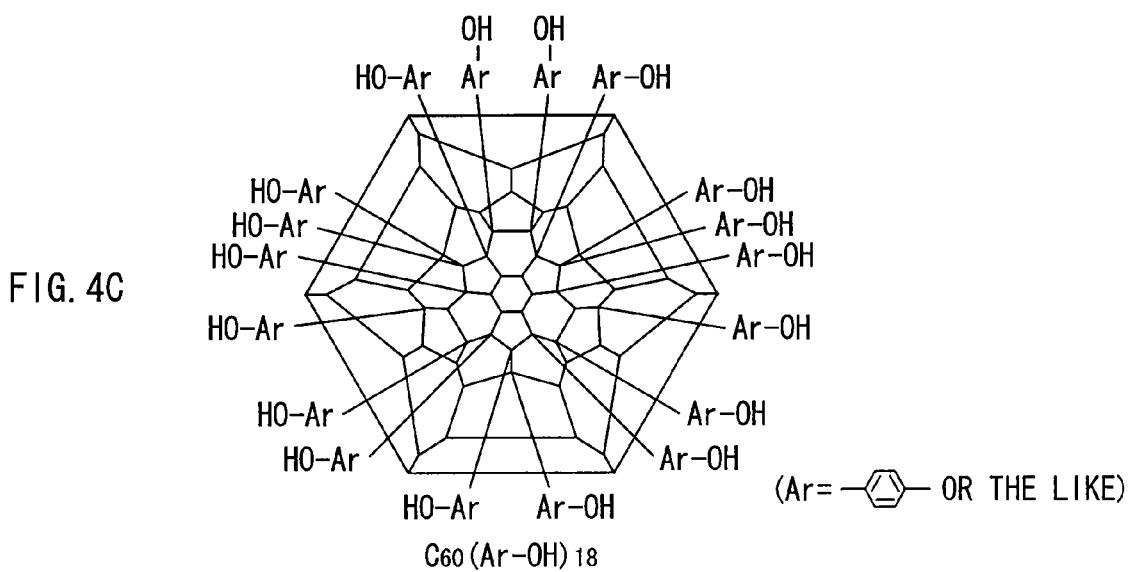

FIG. 4A shows an example of the second producing method of the invention and $C_{60}(Ar—OH)_5Cl$ which can be obtained thereby, and FIGS. 4B and 4C show $C_{70}(Ar—OH)_{10}$ and $C_{60}(Ar—OH)_{18}$ which can be obtained in the same manner, respectively. For example, phenolated fullerene can be further sulfonated by sulfuric acid, as shown in FIG. 1.

Figure 5:
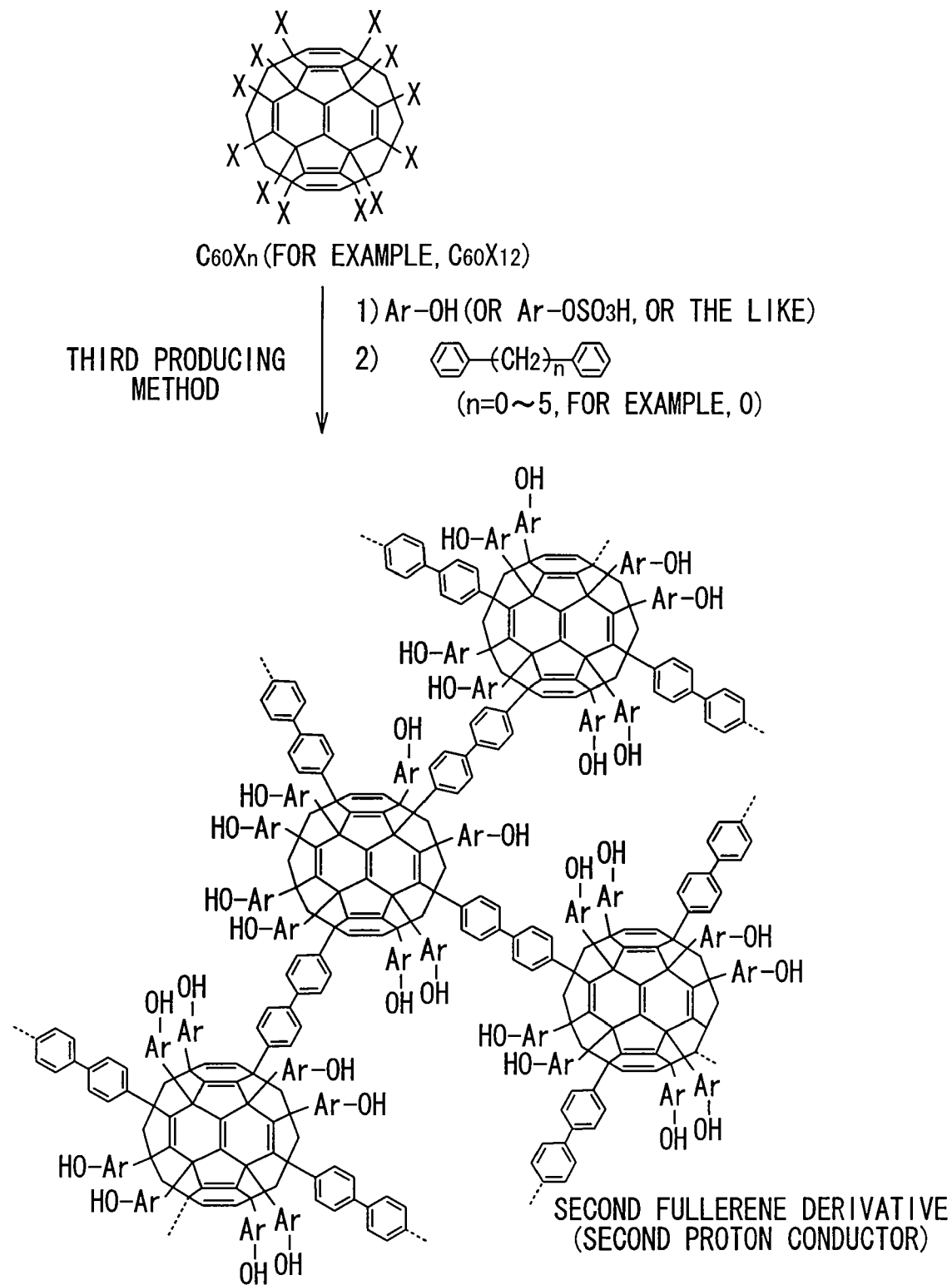
FIG. 5 is an illustration showing a third producing method of the invention and an example of a polymerized fullerene derivative obtained by the third producing method.

FIG. 5 shows a third producing method of the invention and an example of a second fullerene derivative (a second proton conductor) which can be obtained thereby.

The third producing method of the invention is a method of producing a polymerized fullerene derivative as a proton conductor, in which by a reaction among halogenated fullerene which is produced based on the above first producing method of the invention, a first aromatic compound having one or more proton dissociative group and a second aromatic compound (specifically in the presence of the Lewis acid catalyst), one or more aromatic group of the first aromatic compound having the proton dissociative group is introduced into at least one carbon atom of the fullerene molecule, and a plurality of fullerene derivatives obtained thereby are bonded to one another through an aromatic group of the above second aromatic compound (introduction of the aromatic group by the same nucleophilic substitution reaction as the above).

In the third producing method of the invention, the above reaction can occur in a common system (for example, in a single container), and the number of proton transfer sites in the fullerene derivative obtained by polymerization can be determined by a ratio of the first and the second aromatic compounds. Moreover, the third producing method may adopt a two-step reaction in which a reaction between the above halogenated fullerene and the above first aromatic compound is carried out at first (in this case, a predetermined number of halogen atoms required for a polymer are left in the fullerene molecule), and then a reaction with the above second aromatic compound is carried out to produce the polymerized fullerene derivative.

Further, a Lewis acid catalyst used in the producing method is not specifically limited, and, for example, a catalyst selected from the group consisting of $AlCl_3$, $FeCl_3$ and $TiCl_4$ is cited.

As the above first aromatic compound, an aryl compound such as phenol may be used, and an aromatic compound having one, or two or more hydroxyl groups or the like in one aromatic ring may be used. When an aromatic compound having two or more hydroxyl groups or the like (for example, resorcinol) is used, proton transfer sites can be easily increased.

Moreover, the above first aromatic compound or a mixture of the first aromatic compound and other solvent (for example, o-dichlorobenzene) may be used as a solvent.

As the above second aromatic compound, an aromatic compound represented by Chemical Formula 1 is preferably used. In Chemical Formula 1, n, p and q are integers selected from the range from 0 to 5, and $Ar^1$ and $Ar^2$ are substituted or unsubstituted aryl groups which are the same as or different from each other, and Y and Z are substituted groups which are the same as or different from each other, such as, for example, the above-described proton dissociative hydroxyl group or the like.

Moreover, a large number of the above fullerene derivatives can be three-dimensionally bonded to one another by the aromatic group of the above second aromatic compound so as to be polymerized. Further, the structure of the above second aromatic compound as a chain for bonding between the fullerene derivatives is not limited to the structure of an aromatic compound in which $Ar^1$ and $Ar^2$ are unsubstituted groups (for example, benzene ring group) in Chemical Formula 1, and various structures such as, for example, a structure in which one or more hydroxyl groups are introduced into a benzene ring can be applicable. In the latter case, there is a possibility that proton transfer sites can be increased even in the second aromatic compound by the hydroxyl groups or the like.

As shown in FIGS. 1, 2A, 2B, 2C, 2D, 4A, 4B and 4C, the first fullerene derivative of the invention obtained based on the above-described second producing method of the invention is a fullerene derivative functioning as a proton conductor, which is produced through introducing one or more aromatic group having one or more proton dissociative group into at least one carbon atom of a fullerene molecule.

In the first fullerene derivative of the invention, the above aromatic group may be an aryl group such as a phenol group, however, when an aromatic group having one, or two or more hydroxyl groups or the like is used, proton transfer sites can be easily increased.

Moreover, the second fullerene derivative of the invention obtained based on the third producing method of the invention is a polymerized fullerene derivative functioning as a proton conductor, which is produced through bonding a plurality of fullerene derivatives to one another by the second aromatic group, as shown in FIG. 5, the plurality of fullerene derivatives being produced through introducing the first aromatic groups having the proton dissociative group into the carbon atom of the fullerene molecule.

In the second fullerene derivative of the invention, the above first aromatic group may be, for example, an aryl group such as a phenol group, however, when an aromatic group having one, or two or more hydroxyl groups or the like is used, proton transfer sites can be easily increased Moreover, the above second aromatic group is preferably an aromatic group represented by Chemical Formula 2. In Chemical Formula 2, n, p' and q' are integers selected from the range from 0 to 5, and $Ar^{1'}$ and $Ar^{2'}$ are substituted or unsubstituted aromatic groups which are the same as or different from each other, and Y and Z are substituted groups which are the same as or different from each other, such as, for example, the above-described proton dissociative hydroxyl group or the like.

Further, the structure of the above second aromatic group as a chain for bonding between the fullerene derivatives is not limited to the structure of an aromatic group in which $Ar^{1'}$ and $Ar^{2'}$ are unsubstituted groups (for example, benzene ring group) in Chemical Formula 2, and various structures such as, for example, a structure in which one or more hydroxyl groups are introduced into a benzene ring can be applicable. In the latter case, there is a possibility that proton transfer sites can be increased even in the second aromatic compound by the hydroxyl groups or the like.

The above polymerized fullerene derivative is preferably polymerized through three-dimensionally bonding a large number of the above fullerene derivatives to one another by the above second aromatic group.

The number of the hydroxyl groups added to the first and the second fullerene derivatives of the invention, or the arrangement of the hydroxyl groups in the molecule can be variously modified, and the fullerene derivative having the hydroxyl groups can be further sulfonated. The sulfonated fullerene derivative can be variously modified, such as a sulfonated fullerene derivative having a sulfone group only in one molecule, or a sulfonated fullerene derivative into which one, or a plurality of sulfone groups and one, or a plurality of hydroxyl groups are introduced, or the like.

The first and the second proton conductors of the invention may substantially comprise the above fullerene derivative only, or may comprise the fullerene derivatives bonded by a binder.

Figure 6A:
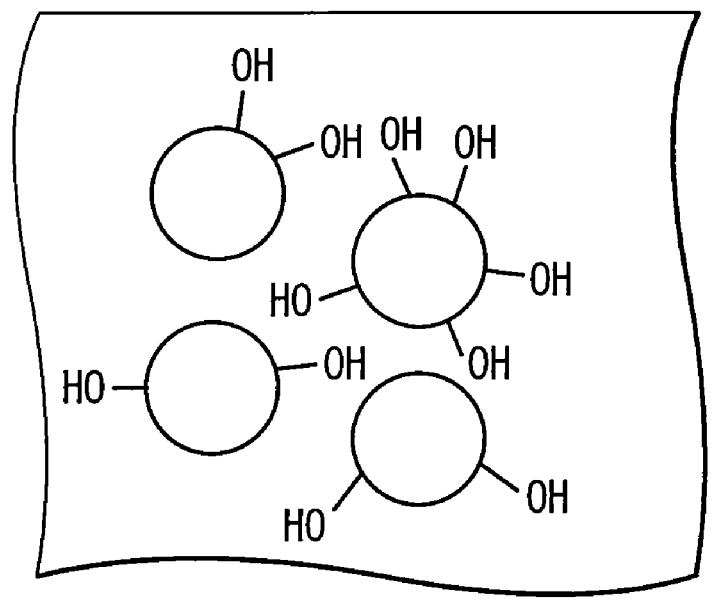
FIGS. 6A and 6B are schematic views showing examples of a proton conductor of the invention.

As shown in a schematic view of FIG. 6A, it has been found that in an aggregate of fullerenol obtained based upon the first producing method of the invention, an interaction among hydroxyl groups of fullerenol molecules adjacent to one another (in the drawing, ○ indicates a fullerene molecule) occurs, thereby the aggregate exhibits high proton conductivity (in other words, dissociation of $H^+$ from phenolic hydroxyl groups of the fullerenol molecules) as a macro aggregate.

Figure 6B:
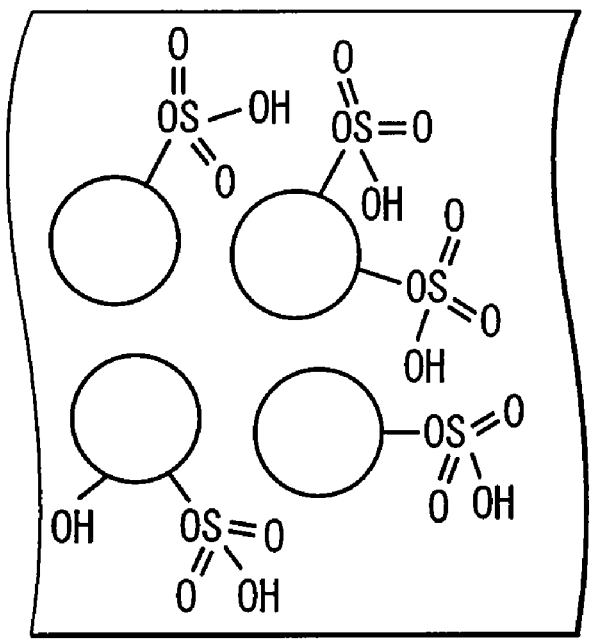

Further, except for fullerenol, for example, a fullerene derivative having a plurality of sulfone groups shown in FIG. 6B can be used as an aggregate.

Moreover, the proton dissociative group of the invention is not limited to the above hydroxyl group and the sulfone group, and is selected from the group consisting of —OH, —$OSO_3H$, —COOH, —$SO_3H$ and —$OPO(OH)_2$, for example.

Further, in the invention, in order to produce a fullerenol derivative, the halogenated fullerene is used as a precursor, so a large number of proton dissociative groups which are at least one selected from the group consisting of OH groups, $SO_3H$ groups, aromatic groups containing hydroxyl groups and so on can be introduced into one fullerene molecule, thereby a number density of proton transfer sites per volume in the proton conductor increases. Further, in order to exhibit dependence in properties of halogen, the number and the position of added proton dissociative groups can be specifically determined.

Further, proton conductivity becomes more pronounced when sulfone groups, instead of hydroxyl groups, are introduced into the carbon atom of the fullerene molecule.

When the number of the hydroxyl groups or the like added to the fullerene molecule increases, the proton conductivity of the obtained fullerene derivative may become higher, and the strength thereof may become lower. However, as in the case of the second fullerene derivative of the invention, when the fullerene derivative is polymerized, while maintaining high proton conductivity, the strength can be enhanced.

The first and the second proton conductors of the invention (the first and the second fullerene derivatives of the invention) can be preferably used in various electrochemical devices.

In other words, the first or the second proton conductor can be preferably used in a basic structure comprising a first electrode, a second electrode and a proton conductor sandwiched between the electrodes.

More specifically, the first or the second proton conductor of the invention can be preferably used in an electrochemical device in which at least one of the first electrode and the second electrode is a gas electrode, or an electrochemical device in which at least one of the first electrode and the second electrode is an active material electrode.

In this case, it is preferable that the proton conductor substantially comprises the above fullerene derivative only, or comprises the fullerene derivatives bonded by a binder.

An example of a fuel cell in which the proton conductor substantially comprising the above fullerene derivatives only is used will be described below.

Figure 7:
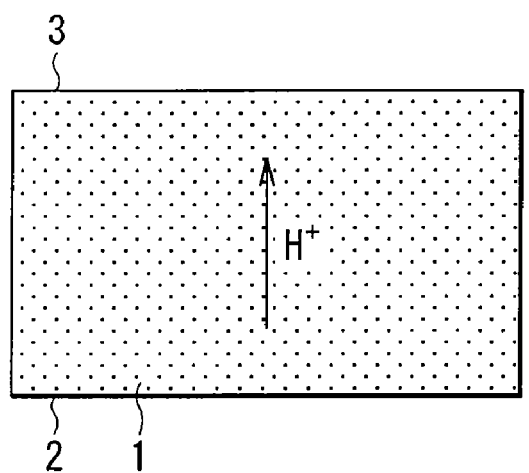
FIG. 7 is an illustration showing the structure of a fuel cell according to an embodiment of the invention.

Proton conduction in the fuel cell is as shown in a schematic view of FIG. 7. A proton conducting portion 1 is sandwiched between a first electrode (for example, hydrogen electrode) 2 and a second electrode (for example, oxygen electrode) 3, and dissociated protons move from the first electrode 2 side to the second electrode 3 side along a direction indicated by an arrow in the drawing.

Figure 8:
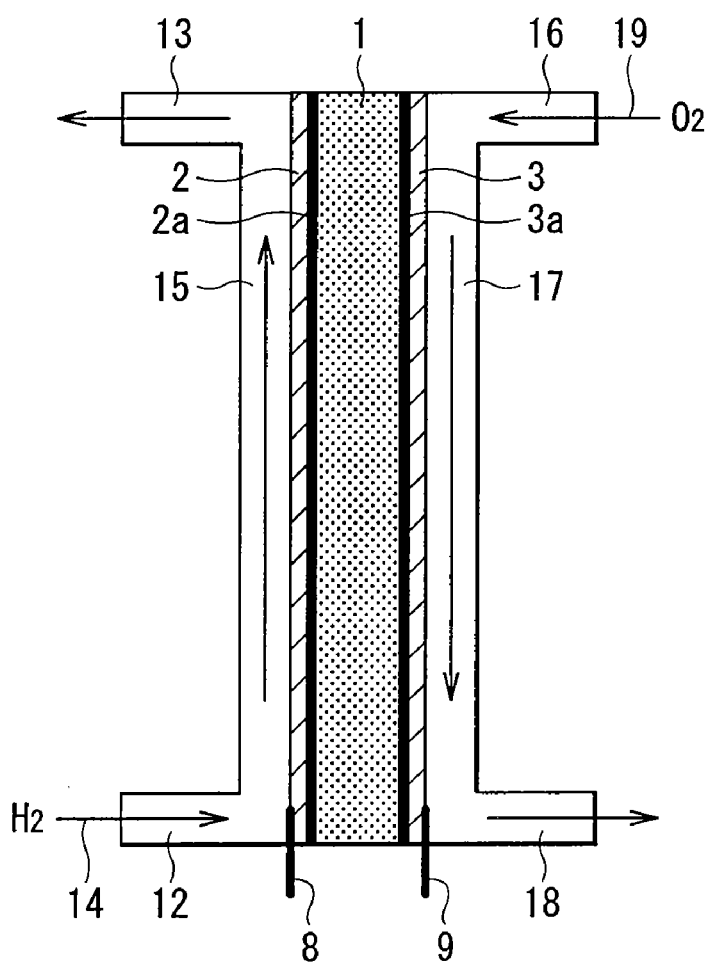
FIG. 8 is a sectional view of the fuel cell shown in FIG. 7.

FIG. 8 shows a specific example of a fuel cell using the first or the second proton conductor of the invention as a proton conducting portion.

The fuel cell comprises an anode (fuel electrode or hydrogen electrode) 2 with a terminal 8 and a cathode (oxygen electrode) 3 with a terminal 9 which face each other, and catalysts 2a and 3b are in contact with or dispersed in the anode 2 and the cathode 3, respectively. A film-shaped proton conducting portion 1 which is formed through compression molding of the fullerene derivative is sandwiched between the anode 2 and the cathode 3.

During use of the fuel cell, on the anode 2 side, hydrogen is supplied from an inlet 12, and is discharged from an outlet 13 (which is not provided in some cases). While fuel ($H_2$) 14 passes through a flow path 15, protons are generated, and the protons move to the cathode 3 side together with protons generated in the proton conducting portion 1. Then, the protons are reacted with oxygen (air) 19 which is supplied from an inlet 16 to a flow path 17 so as to direct to an outlet 18. Thereby a desired electromotive force can be generated.

In the fuel cell with such a structure, while protons are dissociated in the proton conducting portion 1, protons supplied from the anode 2 side move to the cathode 3 side, so proton conductivity becomes higher. Accordingly, no humidifier or the like is required, thereby simplification of the system and a reduction in the weight of the system can be achieved.

The second proton conductor of the invention comprises the above polymerized fullerene derivative, so the proton conductor has a film forming ability, therefore the proton conductor can form the proton conducting portion without binder, and can overcome a film weakening due to the hydroxyl groups or the like of the fullerene derivative. On the other hand, the first proton conductor of the invention can not only form a proton conducting portion through compression molding (aggregate) but also form a proton conducting portion with sufficient strength through bonding by a binder.

In this case, as a high molecular weight material which can be used as a binder, one kind, or two or more kinds of known polymers having film-forming properties are used, and the binder content in the proton conducting portion is generally limited to 20 wt % or less. It is because when the content exceeds 20 wt %, proton conductivity may decline.

The proton conducting portion with such a structure includes a fullerene derivative as a proton conductor, so the same proton conductivity as that of the above-described proton conductor substantially comprising the fullerene derivative only can be exhibited.

In addition, unlike the case where the proton conductor comprises the fullerene derivative only, the proton conductor has film-forming properties derived from the high molecular weight material, and the proton conductor can be used as a flexible proton conductive thin film (with a thickness of 300 µm or less, in general) having larger strength and a gas penetration prevention function, compared to a compression-molded product made of powder of the fullerene derivative.

Further, the above high molecular weight material is not specifically limited, as long as the high molecular weight material causes as little obstruction to proton conductivity (due to a reaction with the fullerene derivative, or the like) as possible, and has film-forming properties. In general, a high molecular weight material having no electronic conductivity and having excellent stability is used. As specific examples of the high molecular weight material, polyfluoroethylene, polyvinylidene fluoride, polyvinyl alcohol and so on are cited, and they are preferable high molecular weight materials because of the following reasons.

Firstly, polyfluoroethylene is preferable because, compared to other high molecular weight materials, a thin film with larger strength can be formed with a small amount of the polyfluoroethylene content. The content in this case is as small as 3 wt % or less, preferably as small as within a range from 0.5 wt % to 1.5 wt %, and the thin film can have as thin a thickness as within a range from 100 µm to 1 µm in general.

Next, polyvinylidene fluoride and polyvinyl alcohol are preferable because a proton conductive thin film having a superior gas penetration prevention function can be formed by using polyvinylidene fluoride or polyvinyl alcohol. The content thereof in this case may be within a range from 5 wt % to 15 wt %.

In any case of polyfluoroethylene, polyvinylidene fluoride or polyvinyl alcohol, the content thereof which is less than the lower limit of the range may adversely affect film formation.

In order to obtain a thin film of the proton conducting portion formed through bonding each fullerene derivative of the invention by a binder, a known method such as compression molding, extrusion molding or the like may be used.

Figure 12:
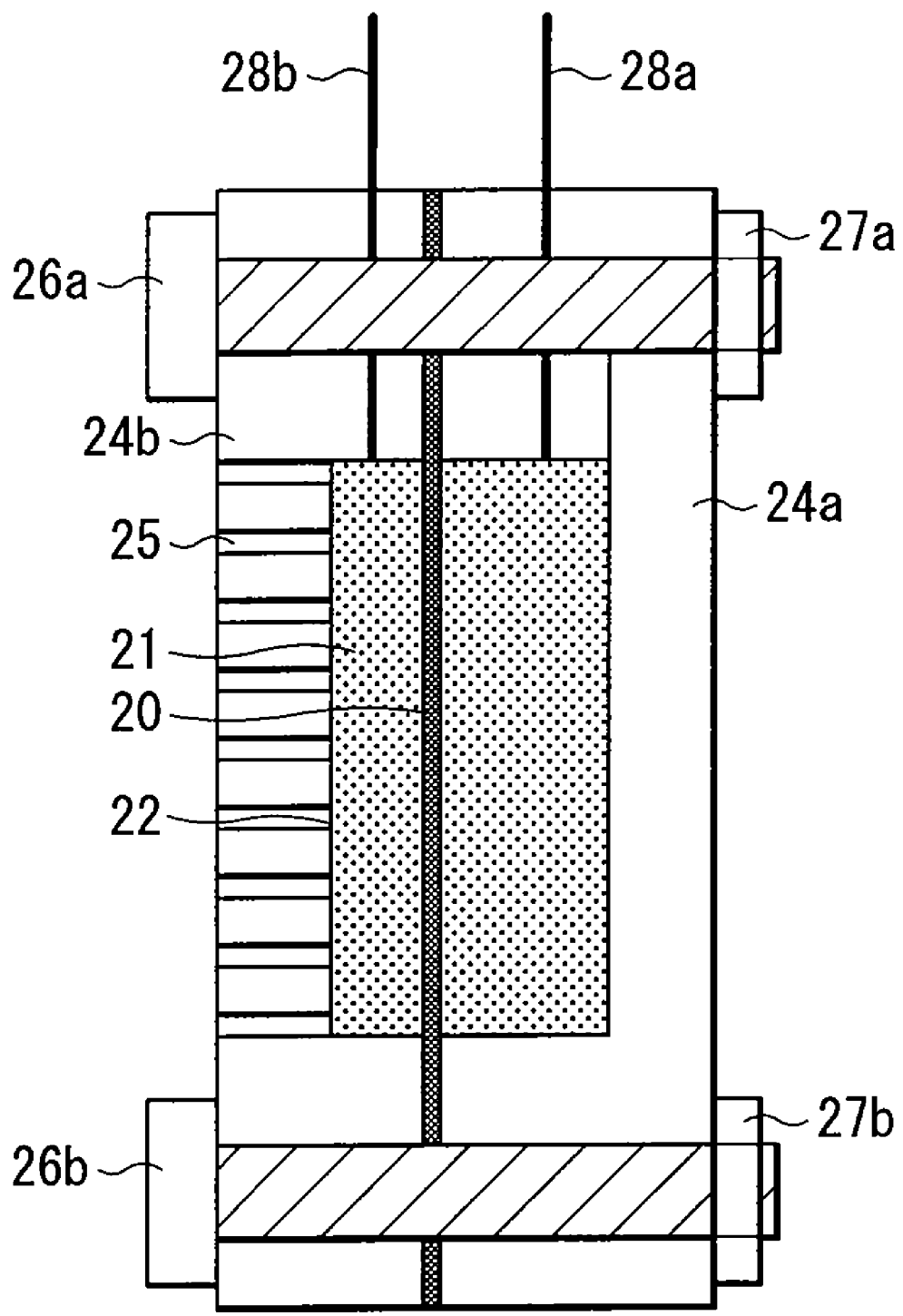
FIG. 12 is an illustration showing the structure of a hydrogen-air cell according to the embodiment of the invention.

FIG. 12 shows a hydrogen-air cell to which the present invention is applicable. In the hydrogen-air cell, a hydrogen electrode 21 and an air electrode 22 faces each other with a thin-film-shaped proton conductor (proton conductor made of the fullerene derivative of the invention only or a mixture of the fullerene derivative of the invention and a binder) 20 in between, and the outsides of the electrodes 21 and 22 are sandwiched between a Teflon plate 24a, and a Teflon plate 24b with a large number of holes 25. All components are fixed by the bolts 26a and 26b and nuts 27a and 27b. A hydrogen electrode lead 28a and an air electrode lead 28b are laid from the hydrogen electrode 21 and the air electrode 22, respectively, to outside.

Figure 13:
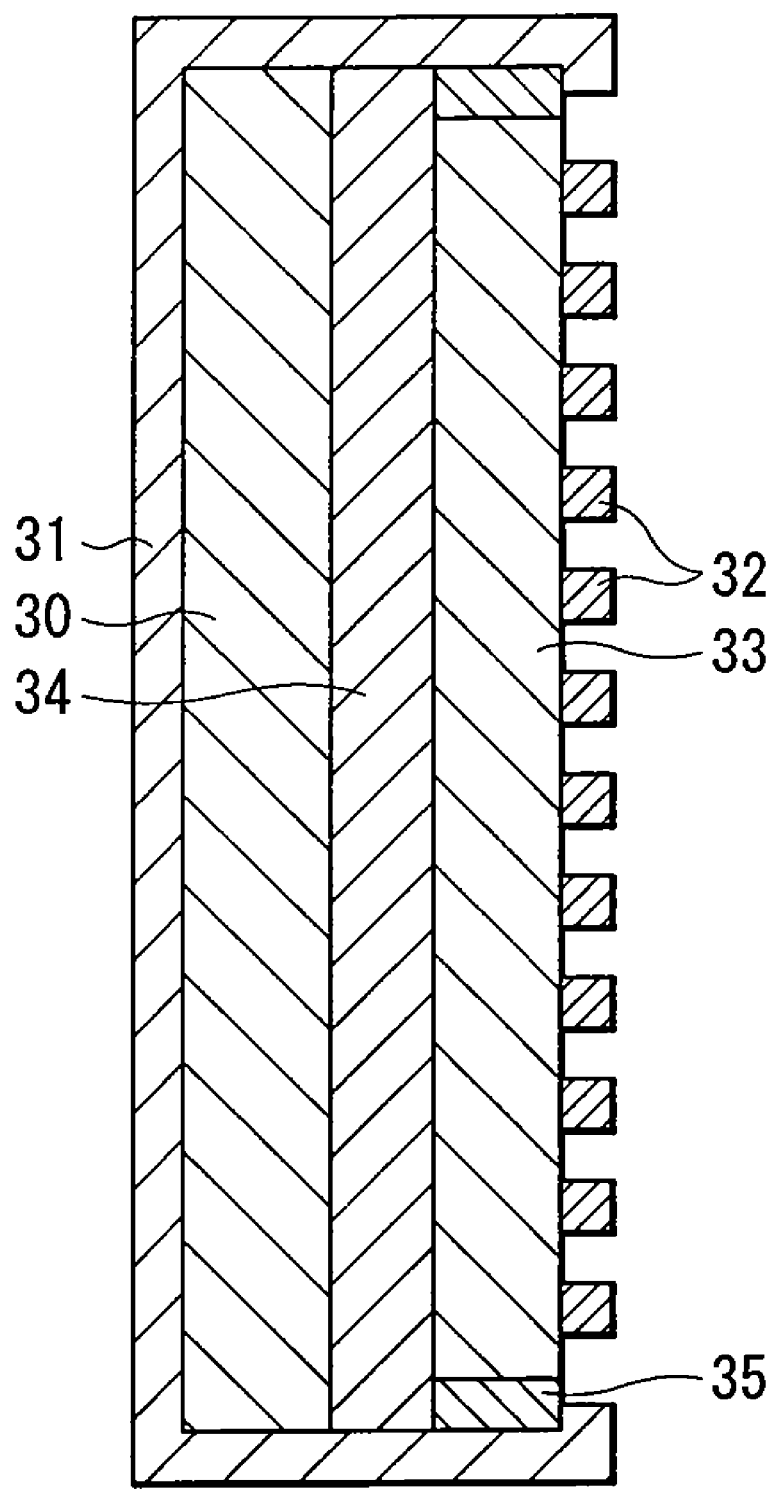
FIG. 13 is a schematic view showing the structure of an electrochemical device according to another embodiment of the invention.

Further, an electrochemical device shown in FIG. 13 can be used as a secondary battery or the like, and the electrochemical device has a structure in which a proton conductor 34 is sandwiched between an anode 31 having an anode active material layer 30 on an internal surface thereof, and a cathode 33 (gas electrode) having a gas penetration support 32 on an outer surface thereof. As the proton conductor 34, a proton conductor made of the fullerene derivative of the invention only or a mixture of the fullerene derivative of the invention and a binder is used. As an anode active material, a hydrogen absorbing alloy, or a carbon material such as fullerene supported by the a hydrogen absorbing alloy is preferable, and as the gas penetration support 32, for example, a porous carbon paper or the like is used. The cathode 33 is preferably formed through coating with, for example, a material which is carbon powder supported by platinum in paste form. Further, a space between the anode 31 and the cathode 33 is sealed by a gasket 35. In the electrochemical device, water is present on the cathode 33 side so as to be capable of charge.

Figure 14:
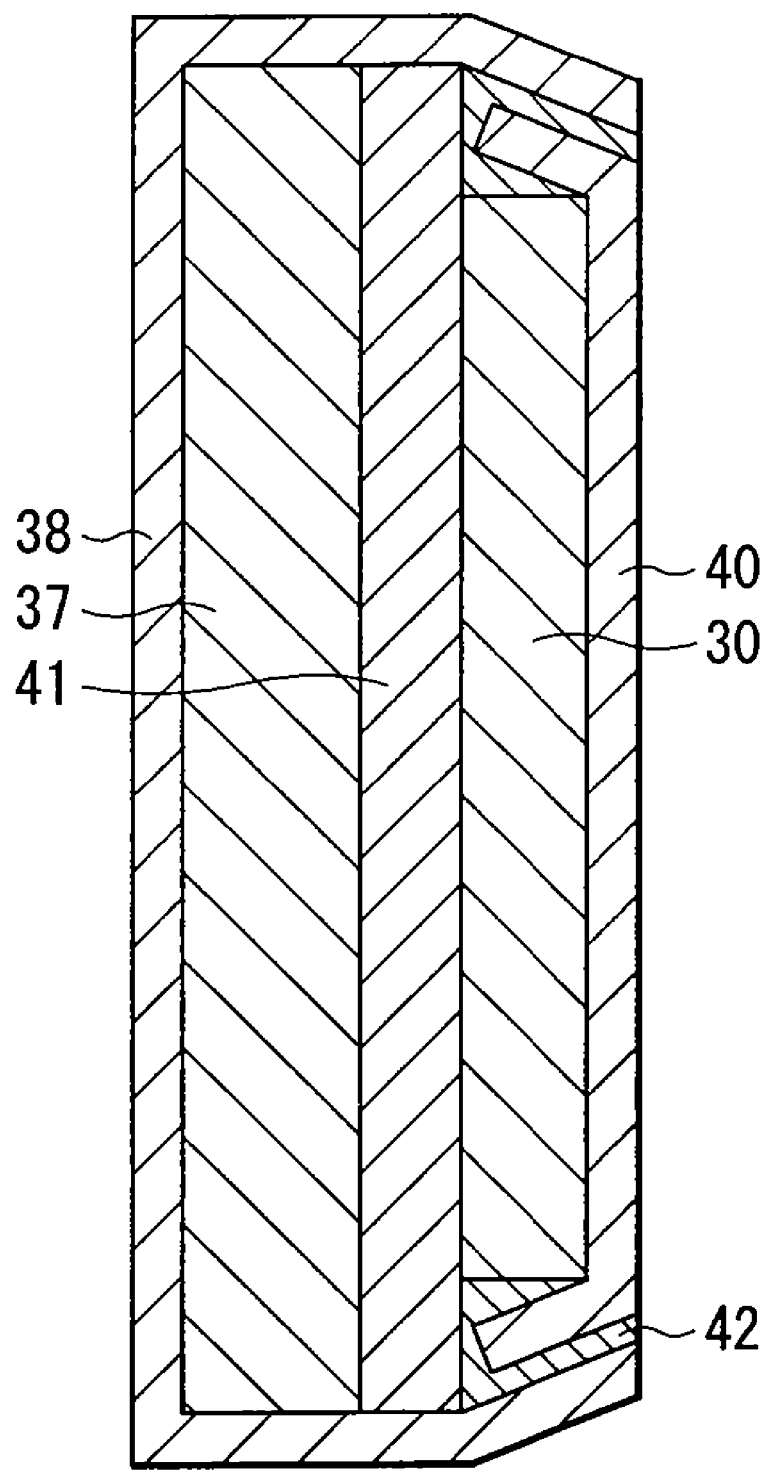
FIG. 14 is a schematic view showing the structure of an electrochemical device according to still another embodiment of the invention.

Further, an electrochemical device shown in FIG. 14 can be used as a secondary battery or the like, and the electrochemical device has a structure in which a proton conductor 41 formed through introducing a binder into each thin-film-shaped fullerene derivative of the invention between an anode 38 having an anode active material layer 37 on an internal surface thereof, and a cathode 40 having a cathode active material layer 39 on an internal surface thereof. As a cathode active material, for example, a material mainly containing nickel hydroxide is used. Further, in the electrochemical device, a space between the anode 38 and the cathode 40 is sealed with a gasket 42.

Any of the electrochemical devices shown in FIGS. 12, 13 and 14 can exert a proton conducting effect in the same mechanism as that of the electrochemical devices shown in FIGS. 7 and 8, which use the proton conductor substantially comprising each fullerene derivative of the invention only. In addition, when the proton conductor comprises the fullerene derivative in combination with a high molecular weight material having film-forming properties, the proton conductor can be used in a form of thin film with improved strength and small gas permeability, so excellent proton conductivity can be exhibited.

The present invention will be described below with reference to Examples.

<Synthesis 1 of Halogenated Fullerene (Precursor)>

The synthesis of halogenated fullerene was carried out referring to a document of "Paul R. Birkett et al., Nature 1992, 357, 479".

A fullerene molecule ($C_{60}$) and bromine ($Br_2$) were reacted with each other in carbon tetrachloride so as to produce a peach bloom compound in a plate shape (a yield thereof was 92%). When the compound was subjected to a FT-IR measurement, the IR spectrum of the compound nearly conformed to that of $C_{60}Br_6$ shown in the above document, therefore, it was confirmed that the compound was a target material, that is, brominated fullerene ($C_{60}Br_6$).

<Fullerene Derivative: Synthesis 1 of Polyhydroxylated Fullerene>

The halogenated fullerene ($C_{60}Br_6$) obtained by the above reaction was reacted with hydroxide (NaOH) in an inert solvent which was o-dichlorobenzene (ODCB) with $AlCl_3$ as Lewis acid added thereto at room temperature so as to obtain polyhydroxylated fullerene (fullerenol) ($C_{60}(OH)_6$).

<Production 1 of Fullerene Derivative Aggregate Pellet>

Next, 90 mg of powder of fullerenol obtained by the above reaction was pressed in one direction so as to be formed in a 15 mm-diameter circular pellet. A pressing pressure at that time was approximately 7000 $kg/cm^2$. As a result, in spite of the fact that the fullerenol powder included no binder resin or the like, the powder had excellent moldability, so the powder could be easily pelletized. The pellet had a thickness of approximately 300 μm (microns). The pellet was taken as a pellet of Example 1.

<Synthesis 2 of Halogenated Fullerene (Precursor)>

The synthesis of halogenated fullerene was carried out referring to a document of "Olga V. Boltalina et al., J. Chem. Soc. Perkin Trans. 2, 1998, 649".

A mixture containing 25 mg of fullerene molecules ($C_{60}$) and 120 mg of $MnF_3$ was introduced into a nickel tube (with a length of 30 mm and a diameter of 5 mm, one end thereof was closed), and then, the nickel tube was placed in a glass tube. The pressure in the glass tube was reduced, and then the glass tube was filled with argon so that the pressure in the glass tube became 0.5 mbar. The glass tube was heated to 350° C. within 30 minutes, and the temperature of the glass tube was kept at 350° C. for 24 hours. After that, the color of the material was changed from a pale brown to nearly white through orange-yellow, so the material was cooled to obtain white powder. When the white powder was subject to a FT-IR measurement, the IR spectrum of the white powder nearly conformed to that of $C_{60}F_{36}$ shown in the above document, so it was confirmed that the white powder was a target material, that is, fluorinated fullerene ($C_{60}F_{36}$) (a yield thereof was 30%).

<Fullerene Derivative: Synthesis 2 of Polyhydroxylated Fullerene>

The above fluorinated fullerene ($C_{60}F_{36}$) was processed in the same method as that of the above synthesis 1 of the fullerene derivative so as to obtain corresponding polyhydroxylated fullerene (fullerenol) ($C_{60}(OH)_{36}$).

<Production 2 of Fullerene Derivative Aggregate Pellet>

In the same method as that of the above production 1 of the fullerene derivative aggregate pellet, fullerenol synthesized from fluorinated fullerene was formed in a pellet with a thickness of approximately 300 μm. The pellet was taken as a pellet of Example 2.

<Fullerene Derivative: Synthesis 3 of Hydrogensulfate-esterified Fullerene (Whole Esterification)>

The synthesis was carried out referring to a document of "Chiang, L. Y.; Wang, L. Y.; Swirczewski. J. W.; Soled, S.; Cameron, S. J. Org. Chem. 1994, 59, 3960".

After 1 g of powder of fullerenol obtained by the synthesis 1 of the fullerene derivative was put in 60 ml of fuming sulfuric acid, the powder was stirred at room temperature in a nitrogen atmosphere for three days. An obtained reactant was gradually put into anhydrous diethyl ether cooled in a ice bath, and after an obtained deposit was fractionated by centrifugal separation, and the deposit was cleaned with diethyl ether three times and a 2:1 mixture of diethyl ether and acetonitrile two times, then the deposit was dried at 40° C. under a reduced pressure. When powder thus obtained was subjected to a FT-IR measurement, the IR spectrum of the powder nearly conformed to that of hydrogensulfate-esterified fullerenol in which all hydroxyl groups were hydrogensulfate-esterified, shown in the above document, so it was confirmed that the powder was a target material, that is, $C_{60}(OSO_3H)_6$.

<Fullerene Derivative: Production 3 of Hydrogensulfate-esterified Fullerene Aggregate Pellet>

Next, 70 mg of powder of hydrogensulfate-esterified fullerenol was pressed in one direction so as to be formed in a 15 mm-diameter circular pellet. A pressing pressure at that time was approximately 7000 $kg/cm^2$. As a result, in spite of the fact that the powder included no binder resin or the like, the powder had excellent moldability, so the powder could be easily pelletized. The pellet had a thickness of approximately 300 μm. The pellet was taken as a pellet of Example 3.

<Fullerene Derivative: Synthesis 4 of Hydrogensulfate-esterified Fullerene (Partial Esterification)>

After 30 ml of fuming sulfuric acid was added to 2 g of powder of fullerenol obtained by the synthesis 1 of the fullerene derivative, hydroxyl groups contained in the fullerenol were partially esterified.

<Fullerene Derivative: Production 4 of Hydrogensulfate-esterified Fullerene Aggregate Pellet>

Next, 80 mg of powder of the partially hydrogensulfate-esterified fullerenol was pressed in one direction so as to be formed in a 15 mm-diameter circular pellet. A pressing pressure at that time was approximately 7000 kg/cm$^2$. As a result, in spite of the fact that the powder included no binder resin or the like, the powder had excellent moldability, so the powder could be easily pelletized. The pellet had a thickness of approximately 300 μm. The pellet was taken as a pellet of Example 4.

<Synthesis 3 of Halogenated Fullerene (Precursor)>

The synthesis was carried out referring to a document of "Paul R. Birkett et al., J. Chem. Soc. Chem. Commun., 1995, 683".

A solution containing 150 mg of iodine-chloride in 5 ml of dry benzene was added to a solution containing 46.6 mg of fullerene molecules ($C_{60}$) in 60 ml of dry benzene. The mixed solution was stirred, and was left standing for three days at room temperature. Next, a solvent and iodine were removed under a reduced pressure so as to leave 60.7 mg of an orange microcrystalline solid. The product was cleaned with pentane, and after cleaning, the product was heated to 60° C. After the pressure was reduced to 0.1 mmHg, and the temperature of the product was kept at the temperature for 5 hours, dark orange crystal was obtained.

When the obtained crystal was subjected to a FT-IR measurement, the IR spectrum of the crystal nearly conformed to that of $C_{60}Cl_6$ shown in the above document, so it was confirmed that the crystal was a target material, that is, chlorinated fullerene ($C_{60}Cl_6$).

<Synthesis 5 of Fullerene Derivative>

The above obtained halogenated fullerene ($C_{60}Cl_6$) was reacted with phenol ($C_6H_5OH$) in o-dichlorobenzene (ODCB) in the presence of a Lewis acid catalyst ($AlCl_3$) at room temperature, and as a result, a fullerene derivative $C_{60}(C_6H_4OH)_5Cl$ or $C_{60}(C_6H_4OH)_6$ was obtained.

<Production 5 of Fullerene Derivative Aggregate Pellet>

Next, 90 mg of powder of the fullerene derivative was pressed in one direction so as to be formed in a 15 mm-diameter circular pellet. A pressing pressure at that time was approximately 7000 kg/cm$^2$. As a result, in spite of the fact that the powder included no binder resin or the like, the powder had excellent moldability, so the powder could be easily pelletized. The pellet had a thickness of approximately 300 μm. The pellet was taken as a pellet of Example 5.

<Fullerene Derivative: Synthesis 6 of Hydrogensulfate-esterified Fullerene Derivative (Whole Esterification)>

When fuming sulfuric acid was added to the fullerene derivative $C_{60}(C_6H_4OH)_5Cl$ or $C_{60}(C_6H_4OH)_6$ obtained by the synthesis 5 of the fullerene derivative so that all hydroxyl groups added to the fullerene derivative were esterified, a hydrogensulfate-esterified fullerene derivative $C_{60}(C_6H_4OSO_3H)_5Cl$ or $C_{60}(C_6H_4OSO_3H)_6$ was obtained.

<Fullerene Derivative: Production 6 of Hydrogensulfate-esterified Fullerene Derivative Aggregate Pellet>

Next, 70 mg of powder of the hydrogensulfate-esterified fullerene derivative was pressed in one direction so as to be formed in a 15 mm-diameter circular pellet. A pressing pressure at that time was approximately 7000 kg/cm$^2$. As a result, in spite of the fact that the powder included no binder resin or the like, the powder had excellent moldability, so the powder could be easily pelletized. The pellet had a thickness of approximately 300 μm. The pellet was taken as a pellet of Example 6.

<Synthesis 7 of Fullerene Derivative>

The hologenated fullerene ($C_{60}Cl_6$) obtained by the above synthesis 5 of the halogenated fullerene precursor was reacted with resorcinol ($C_6H_4(OH)_2$) in o-dichlorobenzene (ODCB) in the presence of a Lewis acid catalyst ($AlCl_3$) at room temperature. As a result, a fullerene derivative $C_{60}(C_6H_4(OH)_2)_5Cl$ or $C_{60}(C_6H_4(OH)_2)_6$ was obtained.

<Production 7 of Fullerene Derivative Aggregate Pellet>

Next, 90 mg of powder of the fullerene derivative was pressed in one direction so as to be formed in a 15 mm-diameter circular pellet. A pressing pressure at that time was approximately 7000 kg/cm$^2$. As a result, in spite of the fact that the powder of the polyhydroxylated fullerene included no binder resin or the like, the powder had excellent moldability, so the powder could be easily pelletized. The pellet had a thickness of approximately 300 μm. The pellet was taken as a pellet of Example 7.

<Fullerene Derivative: Synthesis 8 of Hydrogensulfate-esterified Fullerene Derivative (Whole Esterification)>

When fuming sulfuric acid was added to the fullerene derivative $C_{60}(C_6H_4(OH)_2)_5Cl$ or $C_{60}(C_6H_4(OH)_2)_6$ obtained by the synthesis 6 of the fullerene derivative so that all hydroxyl groups added to the fullerene derivative were esterified, a hydrogensulfate-esterified fullerene derivative $C_{60}(C_6H_4(OSO_3H)_2)_5Cl$ or $C_{60}(C_6H_4(OSO_3H)_2)_6$ was obtained.

<Production 8 of Hydrogensulfate-esterified Fullerene Derivative Aggregate Pellet>

Next, 70 mg of powder of the hydrogensulfate-esterified fullerene derivative was pressed in one direction so as to be formed in a 15 mm-diameter circular pellet. A pressing pressure at that time was approximately 7000 kg/cm$^2$. As a result, in spite of the fact that the powder included no binder resin or the like, the powder had excellent moldability, so the powder could be easily pelletized. The pellet had a thickness of approximately 300 μm. The pellet was taken as a pellet of Example 8.

<Synthesis 4 of Halogenated Fullerene (Precursor)>

After 1.76 g (2.445% 10$^{-3}$ mol) of fullerene molecules ($C_{60}$) were pulverized together with 10.9 g (9.405 % 10$^{-2}$ mol, 38.5 eq.) of $CoF_3$ and 4.29 g (7.3% 10$^{-2}$ mol) of Ni powder (Nilaco, with a particle diameter ranging from 3 μm to 7 μm) in a box, an obtained mixture was put in a stainless container. A sidewall of the stainless container could provide excellent thermal contact. A hole with a diameter of 3 mm was disposed in the above container coated with a stainless sheet, and the container was placed in a quartz tube which had been heated to 50° C. Then, the pressure in the container was reduced to 0.05 mbar, and was heated to 290° C. within 3 hours (1.3° C./min). When the temperature reached 280° C., 80 mbar of argon pressure was added. Next, when the temperature reached 290° C., the temperature was further raised to 350° C. at a rate of 1° C./min. From the time when the temperature reached 290° C., a reactant deposited in a cooled portion of the quartz tube could be observed. Fourteen hours later, heating was stopped, and the temperature of the above container decreased to room temperature, then the reactant deposited in the container, that is, $C_{60}F_{40-44}$ was taken out. The above reactant was a pale yellow or nearly white compound in a powder shape, and its yield was 1.38 g (37.2%).

A result of a spectroscopic analysis on the compound was shown as below.

Mass spectrum (MALDI-TOF, 4-hydroxycinnamic acid, negative mode): 1537.6($C_{60}F_{43}$), 1518.5($C_{60}F_{42}$), 1499.6 ($C_{60}F_{41}$), 1461.5($C_{60}F_{39}$), 1423.5($C_{60}F_{37}$), 1385.6($C_{60}F_{35}$) IR spectrum (KBr): 1621 w, 1166.3 (vs, (C—F)), 1134.1(vs, (C—F)), 877.1(w), 571.1(w), 595.1(w) UV/Vis spectrum (methylene chloride): 325(sh)

<Synthesis 9 of Fullerene Derivative>

When $C_{60}F_{40-44}$ (1.37% 10-3 mol) obtained by the same method as that of the synthesis 4 of the halogenated fullerene was pulverized together with 7.65 g (46 eq.) of $Na_2SO_3$ in the presence of argon in a box by a ball mill for 60 hours, a high water-soluble compound which was not dissolved in a solvent such as methanol or THF (tetrahydrofuran) was obtained. In order to remove excess salt from the reaction mixture, the reaction mixture together with water as an eluate was purified through a silica-gel tower. After the reaction mixture was passed through a cation exchange device (manufactured by Mitsubishi Chemical America Inc., Daion cation exchange resin SK1B, with a column length of approximately 30 cm), water was removed, and thereby, a compound $C_{60}(SO_3H)_nF_m$ (n is within a range from 5 to 7, for example, 6, m is within a range from 10 to 20, for example 15) in which a major portion of the solid was black or dark brawn was obtained, and the product was dried in a vacuum chamber by an oil pump.

Moreover, the above obtained compound $C_{60}(SO_3H)_nF_m$ was further reacted with, for example, hydroxide (NaOH or the like) so that $C_{60}(SO_3H)_n(OH)_m$ as a fullerene derivative could be produced. Further, the above $C_{60}(SO_3H)_n(OH)_m$ was esterified so that $C_{60}(SO_3H)_n(OSO_3H)_m$ or the like as a fullerene derivative could be produced.

<Production 9 of Fullerene Derivative Aggregate Pellet>

Next, 90 mg of powder of the fullerene derivative was pressed in one direction so as to be formed in a 15 mm-diameter circular pellet. A pressing pressure at that time was approximately 7000 kg/cm². As a result, in spite of the fact that the powder of the fullerene derivative included no binder resin or the like, the powder had excellent moldability, so the powder could be easily pelletized. The pellet had a thickness of approximately 300 μm. The pellet was taken as a pellet of Example 9.

<Synthesis 10 of Polymerized Fullerene Derivative>

Chlorinated fullerene $C_{60}Cl_2$ obtained by the same method as that of the synthesis 3 of the halogenated fullerene was reacted with phenol ($C_6H_4OH$) and biphenyl in the presence of a Lewis acid catalyst ($AlCl_3$) in o-dichlorobenzene so that a polymerized fullerene derivative (a polymer in which $C_{60}$ ($C_6H_4OH)_8$ as a monomer was bonded by biphenyl groups) was obtained. The polymerized fullerene derivative was pelletized, and the pelletized fullerene derivative was a pellet of Example 10.

<Production of Fullerene Aggregate Pellet as Comparison>

For comparison, 90 mg of powder of fullerene $C_{60}$ used as a synthesis material in the above examples was pressed in one direction so as to be formed in a 16 mm-diameter circular pellet. A pressing pressure at that time was approximately 7000 kg/cm². As a result, in spite of the fact that the powder included no binder resin or the like, the powder had excellent moldability, so the powder could be easily pelletized. The pellet had a thickness of approximately 300 μm. The pellet was taken as a pellet of Comparative Example 1.

<Synthesis of Polyhydroxylated Fullerene as Comparison>

For comparison, based on a conventionally known synthesis method (refer to Long Y. Chiang et al. J. Org. Chem. 1994, 59, 3960), 2 g of powder of a $C_{60}/C_{70}$ fullerene mixture containing approximately 15% of $C_{70}$ was put in 30 ml of fuming sulfuric acid, and the powder was stirred for three days while being kept at 57° C. in a nitrogen atmosphere. An obtained reactant was gradually put into anhydrous diethyl ether cooled in a ice bath, and after an obtained deposit was fractionated by centrifugal separation, and the deposit was cleaned with diethyl ether three times and a 2:1 mixture of diethyl ether and acetonitrile two times, then the deposit was dried at 40° C. under a reduced pressure. Further, the dried deposit was put in 60 ml of ion exchange water, and was stirred for 10 hours at 85° C. through bubbling by nitrogen. After a deposit was fractionated by centrifugal separation, and was further cleaned with pure water a few times, and centrifugal separation was repeated, the reactant was dried under a reduced pressure at 40° C. When brawn powder thus obtained was subjected to a FT-IR measurement, the IR spectrum of the powder nearly conformed to that of $C_{60}(OH)_{12}$ shown in the document, so it was confirmed that the powder was polyhydroxylated fullerene ($C_{60}(OH)_{12}$).

<Production of Polyhydroxylated Fullerene Aggregate Pellet as Comparison>

Next, 90 mg of powder of the polyhydroxylated fullerene was pressed in one direction so as to be formed in a 15 mm-diameter circular pellet. A pressing pressure at that time was approximately 7000 kg/cm². As a result, in spite of the fact that the powder included no binder resin or the like, the powder had excellent moldability, so the powder could be easily pelletized. The pellet had a thickness of approximately 300 μm. The pellet was taken as a pellet of Comparative Example 2.

<Proton Conductivity Measurement on Pellets Obtained in Examples and Comparative Examples>

In order to measure conductivity of each pellet of Examples 1 through 10 and Comparative Example 1, at first, the pellet was held between aluminum plates with a diameter of 15 mm which was equivalent to that of each pellet, and an AC voltage (amplitude: 0.1 V) at frequencies ranging from 7 MHz to 0.01 Hz was applied to the pellet so as to measure a complex impedance at each frequency. The measurement was carried out under a dry atmosphere.

Figure 9A:
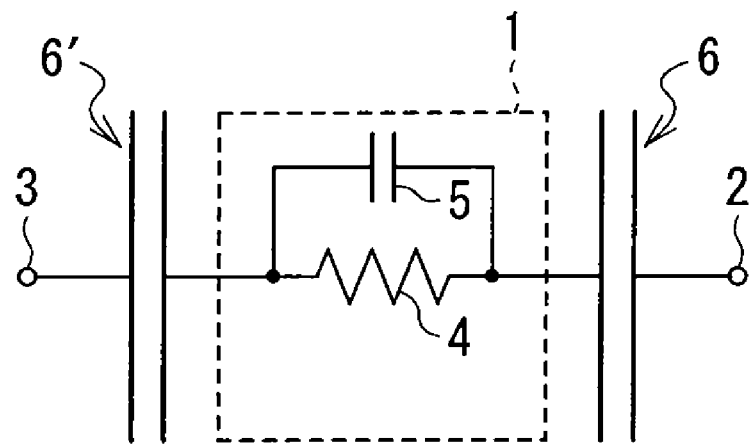
FIGS. 9A and 9B are schematic diagrams of an equivalent circuit of the fuel cell shown in FIG. 7.

In relation to the impedance measurement, the proton conducting portion 1 of a proton conductor made of the above pellet electrically constituted an equivalent circuit as shown in FIG. 9A. In the equivalent circuit, capacitors 6 and 6' were formed between the first electrode 2 and the second electrode 3 with the proton conducting portion 1 indicated by a parallel circuit of a resistor 4 and a capacitor 5 in between. Further, as a delay effect (phase delay at high frequency) during proton transfer occurred by the capacitor 5, the capacitor 5 indicated a parameter of proton transfer, and a proton transfer action occurred by the resistor 4, so the resistor 4 indicated a parameter of mobility.

Herein, a measured impedance Z was represented by $Z=Re(Z)+i \cdot Im(Z)$, and frequency dependence of the proton conducting portion indicated by the above equivalent circuit was measured.

Figure 9B:
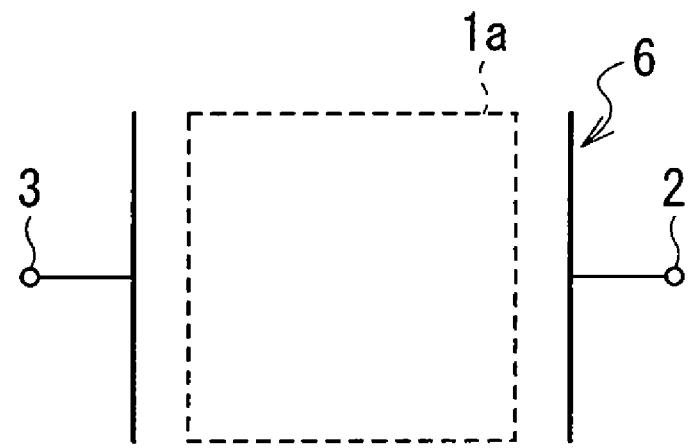

In addition, FIG. 9B shows an equivalent circuit using a typical fullerene molecule without proton dissociation (Comparative Example 1).

Figure 10:
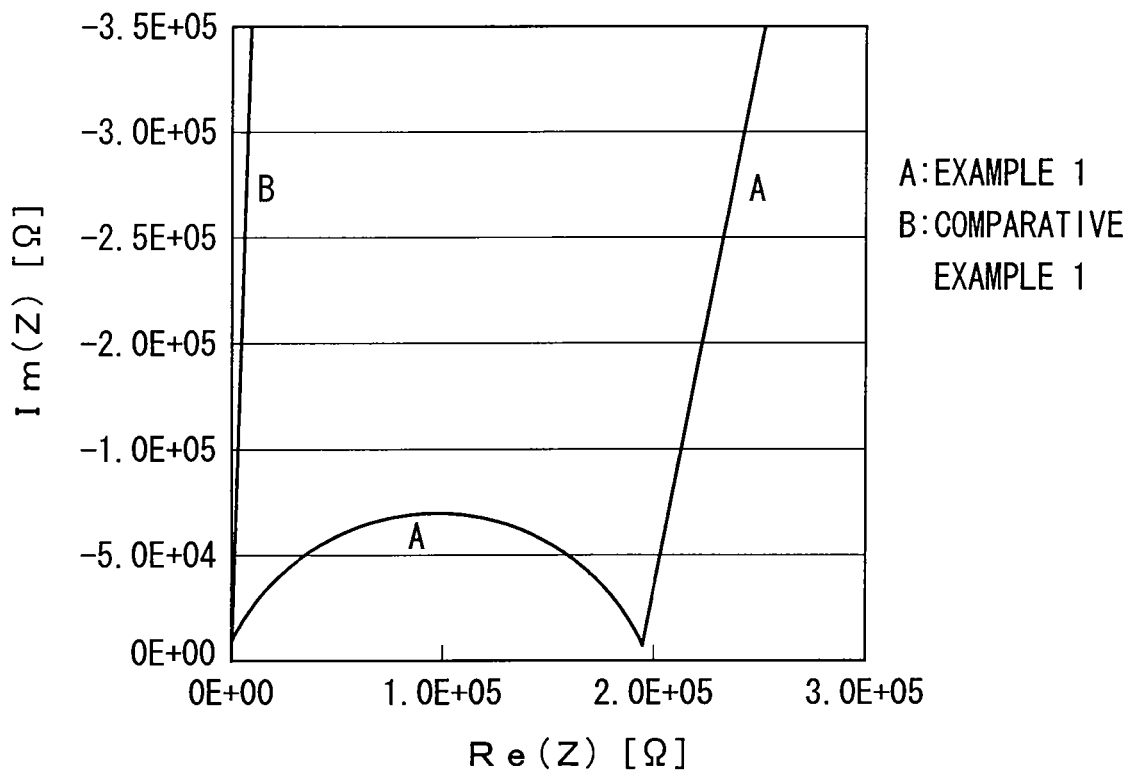
FIG. 10 is a graph showing a result of measuring the complex impedances of a fullerene derivative aggregate pellet used in First Example of the invention.

FIG. 10 shows results of impedance measurement on pellets of Example 1 and Comparative Example 1. In Comparative Example 1, frequency properties of the complex impedance were substantially the same as the behavior of a single capacitor, so a transfer behavior of charged particles (such as electrons, ions or the like) was not observed at all. On the other hand, in Example 1, it was confirmed that in a high frequency region of the impedance, a flattened but very smooth single semicircular arc was shown. It meant that some transfer behavior of charged particles occurred in the pellet. Further, in a low frequency region, a sharp rise in the imaginary part of the impedance was observed. It meant that blocking of charged particles between the pellet and an aluminum electrode occurred, as the voltage gradually became a DC voltage. Herein, the charged particles on the aluminum electrode side were electrons, so it was found that the charged particles in the pellet were not electrons nor holes, but other charged particles, that is, ions. According to the structure of fullerenol used at that time, it was obvious that the charged particles were protons, but not any other charged particles.

The conductivity of the charged particles could be determined by an X-axis intercept of the arc on the high frequency side. In the pellet of Example 1, the conductivity was approximately 5% $10^{-6}$ sec./cm by calculation. Moreover, when the pellets of Examples 2 through 10 were subjected to the same measurement, the frequency properties of the impedance in Examples 2 through 10 were similar in the whole shape to those in Example 1. However, the conductivity of each of Example 2 through 10 determined by an X-axis intercept of the arc was different from others as shown in Table 1. Table 1 shows conductivity of each proton conductor pellet according to the invention (at 25° C.), and, for example, the conductivity was 5% $10^{-2}$ sec./cm in a wet state.

It was evident from Table 1 that when the hydroxyl groups were replaced with $OSO_3H$ groups or $SO_3H$ groups, conductivity in the pellet tended to increase, because hydrogen dissociation was more likely to occur in the $OSO_3H$ groups and the $SO_3H$ groups than the hydroxyl groups. In any case of the hydroxyl groups, the $OSO_3H$ groups and the $SO_3H$ groups, or in a case where two of them were mixed, it was found that protons could be transferred in an aggregate of such a fullerene derivative in a dry atmosphere at room temperature.

Moreover, in Example 2, since, for example, OH groups were excessively introduced into at least one carbon atom of the fullerene molecule, a resonance structure of the above fullerene molecule sometimes became unstable, and alcoholic properties increased. Thereby, the measurement of the conductivity could not be carried out in some cases.

Figure 11:
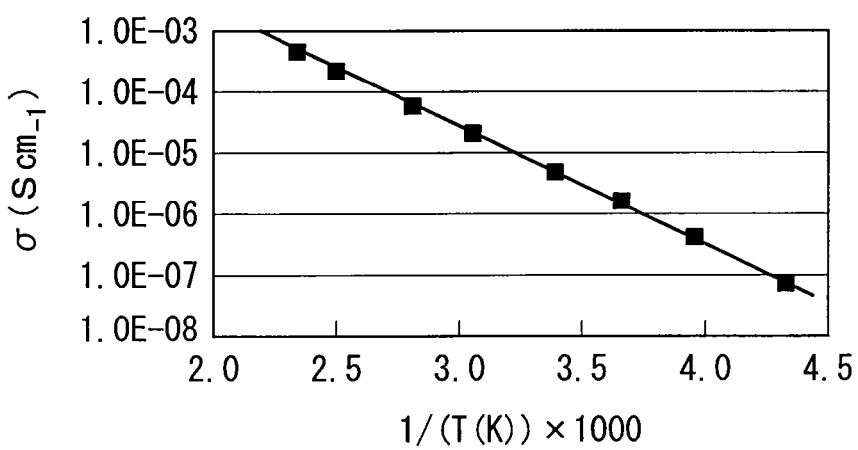
FIG. 11 is a graph showing temperature dependence of proton conductivity of the aggregate pellet shown in FIG. 10.

Next, the pellet of Example 1 was subjected to the above complex impedance measurement within a temperature range from 120° C. to −40° C. so as to determine temperature dependence of the conductivity determined by an arc on the high frequency side. FIG. 11 shows the result as an Arrhenius plot. As shown in FIG. 11, it was extremely obvious that the conductivity was linearly changed according to a change in temperature from 120° C. to −40° C. It meant that a single ion conduction mechanism could occur within the temperature range. In other words, the proton conductor of the invention could have conductivity even in a wide temperature range including room temperature, specifically at a high temperature of 120° C. and a low temperature of −40° C.

As described above, in the producing method of the fullerene derivative of the invention, halogenated fullerene is used as a precursor, so the number and the position of introduced proton dissociative groups added to at least one carbon atom of a fullerene molecule can be controlled, so a larger number of proton dissociative groups can be introduced.

Moreover, the fullerene derivative obtained by the producing method of the fullerene derivative of the invention can exhibit higher proton conductivity, and the electrochemical device of the invention comprising the fullerene derivative is not subject to atmosphere constraints, so downsizing and simplification of the system thereof can be achieved.

Obviously many modifications and variations of the present invention are possible in the light of the above teachings. It is therefore to be understood that within the scope of the appended claims the invention may be practiced otherwise than as specifically described.

The invention claimed is:

1. A method for producing a fullerene derivative as a proton conductor, comprising the steps of:
    reacting a fullerene molecule with at least one halogen atom so as to produce a halogenated fullerene; and
    reacting the halogenated fullerene with a hydroxide or sulfite so as to produce a fullerene derivative as a proton conductor, wherein one or more proton ($H^+$) dissociative group is introduced into at least one carbon atom of the fullerene molecule, wherein,
    the hydroxide is represented as MOH, and the sulfite is represented as $M_2SO_3$ where M is an alkali metal atom.

2. The method of claim 1, wherein
hydroxylated fullerene is obtained by the MOH, and sulfonated fullerene is obtained by the $M_2SO_3$.

3. The method of claim 2, wherein
a hydroxyl group of the hydroxylated fullerene is further inverted into at least one of —$OSO_3H$ and —$OPO(OH)_2$.

4. The method of claim 1, wherein
the fullerene molecule is a spherical carbon cluster molecule Cm where m is any of 36, 60, 70, 76, 78, 80, 82 and 84, or a natural number capable of constituting a cluster molecule.

5. The method of claim 1, wherein
the halogenated fullerene is reacted with the hydroxide or the sulfite in an organic solvent.

6. The method of claim 5, wherein
the organic solvent with at least one of crown ether and a Lewis acid catalyst added thereto is used to react the halogenated fullerene with the hydroxide or the sulfite.

7. The method of claim 5, wherein
at least one of a phase-transfer catalyst and a Lewis acid catalyst is used to react the fullerene derivative with the hydroxide or the sulfite in a two-phase system of a solution of the hydroxide or the sulfite and the organic solvent.

8. The method of claim 1, wherein the halogen atom is selected from the group consisting of a fluorine atom (F), a chlorine atom (Cl) and a bromine atom (Br).

* * * * *